(12) United States Patent
Ebata

(10) Patent No.: US 12,303,330 B2
(45) Date of Patent: May 20, 2025

(54) ULTRASOUND DIAGNOSTIC APPARATUS, METHOD FOR CONTROLLING ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 273 days.

(21) Appl. No.: 17/819,357

(22) Filed: Aug. 12, 2022

(65) Prior Publication Data

US 2022/0378397 A1 Dec. 1, 2022

Related U.S. Application Data

(63) Continuation of application No. PCT/JP2021/006658, filed on Feb. 22, 2021.

(30) Foreign Application Priority Data

Mar. 24, 2020 (JP) ................................ 2020-052260

(51) Int. Cl.
*A61B 8/14* (2006.01)
(52) U.S. Cl.
CPC ..................... *A61B 8/14* (2013.01)
(58) Field of Classification Search
None
See application file for complete search history.

(56) References Cited

U.S. PATENT DOCUMENTS

| | | | |
|---|---|---|---|
| 2007/0004983 A1* | 1/2007 | Chalana | A61B 8/4254 600/443 |
| 2007/0197913 A1* | 8/2007 | Kim | A61B 5/204 600/447 |
| 2010/0331696 A1 | 12/2010 | Kim et al. | |
| 2016/0007972 A1* | 1/2016 | Nishiura | A61B 8/5269 600/437 |
| 2016/0367218 A1* | 12/2016 | Kim | A61B 8/4427 |

(Continued)

FOREIGN PATENT DOCUMENTS

| | | |
|---|---|---|
| JP | 2017-109074 A | 6/2017 |
| JP | 2018-102891 A | 7/2018 |

(Continued)

OTHER PUBLICATIONS

International Search Report issued in PCT/JP2021/006658; mailed Apr. 13, 2021.

(Continued)

*Primary Examiner* — Amal Aly Farag
(74) *Attorney, Agent, or Firm* — Studebaker Brackett PLLC

(57) ABSTRACT

The present application relates to an ultrasound diagnostic apparatus for measuring a urine volume in a urinary bladder of a subject, a method for controlling the ultrasound diagnostic apparatus, and a processor for the ultrasound diagnostic apparatus. The ultrasound diagnostic apparatus includes a urinary bladder extraction unit, a feature quantity calculation unit, a failed frame determination unit, a rescan determination unit, a rescan recommendation unit, a measurement frame selection unit, and a urine volume measurement unit.

18 Claims, 11 Drawing Sheets

(56) References Cited

U.S. PATENT DOCUMENTS

| | | |
|---|---|---|
| 2017/0296148 A1 | 10/2017 | Niemiec et al. |
| 2019/0142390 A1 | 5/2019 | Luo et al. |
| 2019/0183462 A1 | 6/2019 | Yang et al. |
| 2020/0060659 A1 | 2/2020 | Komatsu et al. |
| 2020/0330077 A1 | 10/2020 | Matsumoto |

FOREIGN PATENT DOCUMENTS

| | | |
|---|---|---|
| JP | 2019-076298 A | 5/2019 |
| JP | 2020-028680 A | 2/2020 |
| WO | 2019/163225 A1 | 8/2019 |

OTHER PUBLICATIONS

International Preliminary Report On Patentability (Chapter I) and Written Opinion of the International Searching Authority issued in PCT/JP2021/006658; issued Sep. 22, 2022.

The extended European search report issued by the European Patent Office on Jul. 25, 2023, which corresponds to European Patent Application No. 21775380.5-1126 and is related to U.S. Appl. No. 17/819,357.

\* cited by examiner

ULTRASOUND DIAGNOSTIC APPARATUS, METHOD FOR CONTROLLING ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2021/006658 filed on Feb. 22, 2021, which claims priority under 35 U.S.C. § 119(a) to Japanese Patent Application No. 2020-052260 filed on Mar. 24, 2020. The above application is hereby expressly incorporated by reference, in its entirety, into the present application.

BACKGROUND OF THE INVENTION

1. Field of the Invention

The present invention relates to an ultrasound diagnostic apparatus for measuring a urine volume in a urinary bladder of a subject, a method for controlling the ultrasound diagnostic apparatus, and a processor for the ultrasound diagnostic apparatus.

2. Description of the Related Art

In the related art, an ultrasound diagnostic apparatus is used to observe the urinary bladder of a subject and measure the urine volume in the observed urinary bladder. In general, the urine volume in the urinary bladder of a subject is substantially equal to the volume of the urinary bladder of the subject. Thus, the volume of the urinary bladder of the subject is measured as the urine volume. To perform such urine volume measurement easily, for example, an ultrasound diagnostic apparatus of JP2017-109074A has been developed. In response to a user pressing a trigger button included in the ultrasound diagnostic apparatus of JP2017-109074A in a state in which ultrasound images of a plurality of frames including the urinary bladder of a subject are acquired, the ultrasound diagnostic apparatus automatically selects an ultrasound image of a frame determined to be suitable for urine volume measurement, based on the ultrasound images of the plurality of frames acquired by the user. The ultrasound diagnostic apparatus then measures the urine volume based on the ultrasound image of the selected frame.

SUMMARY OF THE INVENTION

When a user performs a scan of the urinary bladder of a subject while keeping an ultrasound probe in contact with the body surface of the subject, an ultrasound image of a frame not correctly depicting a urinary bladder region may be generated because the ultrasound probe is accidentally separate from the body surface of the subject during the scan. That is, an ultrasound image of a frame suitable for urine volume measurement is not generated, and the scan with an ultrasonic beam may fail. Even when the user fails to perform the scan with the ultrasonic beam, the ultrasound diagnostic apparatus disclosed in JP2017-109074A automatically selects an ultrasound image of a frame to be used in urine volume measurement. Thus, urine volume measurement is performed based on an ultrasound image of a frame not suitable for urine volume measurement. As a result, there is an issue in that the accuracy of urine volume measurement decreases.

The present invention is made to overcome such an issue in the related art, and an object thereof is to provide an ultrasound diagnostic apparatus capable of increasing the accuracy of urine volume measurement, a method for controlling the ultrasound diagnostic apparatus, and a processor for the ultrasound diagnostic apparatus.

To achieve this object, an ultrasound diagnostic apparatus according to the present invention includes an image memory configured to store ultrasound images of a plurality of frames acquired through a scan with an ultrasonic beam on a subject using an ultrasound probe; a urinary bladder extraction unit configured to extract a urinary bladder region from each of the ultrasound images of the plurality of frames; a feature quantity calculation unit configured to calculate a feature quantity related to the urinary bladder region extracted for each of the ultrasound images of the plurality of frames by the urinary bladder extraction unit; a failed frame determination unit configured to determine whether or not each of the ultrasound images of the plurality of frames is of a failed frame for which the scan with the ultrasonic beam on the subject has failed; a rescan determination unit configured to determine whether or not a rescan with an ultrasonic beam is needed, based on a time-series change in the feature quantity calculated by the feature quantity calculation unit and a time-series position of the ultrasound image of the frame determined to be the failed frame by the failed frame determination unit; a rescan recommendation unit configured to recommend the rescan with the ultrasonic beam to a user in a case where the rescan determination unit determines that the rescan with the ultrasonic beam is needed; a measurement frame selection unit configured to select an ultrasound image of a measurement frame that serves as a target subjected to measurement from among the ultrasound images of the plurality of frames, based on the feature quantity calculated by the feature quantity calculation unit in a case where the rescan determination unit determines that the rescan with the ultrasonic beam is not needed; and a urine volume measurement unit configured to analyze the ultrasound image of the measurement frame selected by the measurement frame selection unit to measure a urine volume.

The ultrasound diagnostic apparatus can further include an input device with which the user performs an input operation; and an execution-of-rescan reception unit configured to receive a selection of whether or not to perform the rescan with the ultrasonic beam, in accordance with the input operation performed by the user via the input device in a case where the rescan with the ultrasonic beam is recommended by the rescan recommendation unit. In this case, the measurement frame selection unit can be configured to select an ultrasound image of a measurement frame that serves as a target subjected to measurement from among the ultrasound images of the plurality of frames, based on the feature quantity calculated by the feature quantity calculation unit in a case where the rescan determination unit determines that the rescan with the ultrasonic beam is not needed or in a case where the execution-of-rescan reception unit receives a selection of not performing the rescan with the ultrasonic beam.

The failed frame determination unit can be configured to perform image analysis on each of the ultrasound images of the plurality of frames and determine that the ultrasound image is of a failed frame in a case where a failed region where the ultrasound probe is not in contact with the subject is confirmed in the ultrasound image based on a luminance profile in a depth direction of the ultrasound image.

Alternatively, the failed frame determination unit can be configured to perform image analysis on each of the ultrasound images of the plurality of frames and determine that the ultrasound image is of a failed frame in a case where a failed region where pressing of the ultrasound probe against the subject is insufficient is confirmed in the ultrasound image based on an edge clarity of the urinary bladder region in the ultrasound image.

The rescan determination unit can be configured to determine that the rescan with the ultrasonic beam is not needed in a case where the failed region is confirmed in the ultrasound image by the failed frame determination unit but the urinary bladder region extracted by the urinary bladder extraction unit does not overlap the failed region.

The ultrasound diagnostic apparatus can further include the ultrasound probe; and a pressure sensor attached to the ultrasound probe and configured to detect a contact pressure of the ultrasound probe against the subject. In this case, the failed frame determination unit can be configured to determine whether or not each of the ultrasound images of the plurality of frames is of a failed frame, based on the contact pressure of the ultrasound probe detected by the pressure sensor.

The failed frame determination unit can be configured to notify the user of a portion of the ultrasound probe that is not in contact with the subject or a portion of the ultrasound probe of which pressing against the subject is insufficient.

The ultrasound diagnostic apparatus can further include a warning unit configured to issue a warning to the user in a case where the failed frame determination unit determines that any of the ultrasound images of the plurality of frames is of a failed frame.

A method for controlling an ultrasound diagnostic apparatus according to the present invention includes storing ultrasound images of a plurality of frames acquired through a scan with an ultrasonic beam on a subject using an ultrasound probe; extracting a urinary bladder region from each of the ultrasound images of the plurality of frames; calculating a feature quantity related to the urinary bladder region extracted for each of the ultrasound images of the plurality of frames; determining whether or not each of the ultrasound images of the plurality of frames is of a failed frame for which the scan with the ultrasonic beam on the subject has failed; determining whether or not a rescan with an ultrasonic beam is needed, based on a time-series change in the feature quantity and a time-series position of the ultrasound image of the frame determined to be the failed frame; recommending the rescan with the ultrasonic beam to a user in a case where it is determined the rescan with the ultrasonic beam is needed; selecting an ultrasound image of a measurement frame that serves as a target subjected to measurement from among the ultrasound images of the plurality of frames, based on the feature quantity in a case where it is determined that the rescan with the ultrasonic beam is not needed; and analyzing the ultrasound image of the measurement frame to measure a urine volume.

A processor for an ultrasound diagnostic apparatus according to the present invention is configured to store ultrasound images of a plurality of frames acquired through a scan with an ultrasonic beam on a subject using an ultrasound probe; extract a urinary bladder region from each of the ultrasound images of the plurality of frames; calculate a feature quantity related to the urinary bladder region extracted for each of the ultrasound images of the plurality of frames; determine whether or not each of the ultrasound images of the plurality of frames is of a failed frame for which the scan with the ultrasonic beam on the subject has failed; determine whether or not a rescan with an ultrasonic beam is needed, based on a time-series change in the feature quantity and a time-series position of the ultrasound image of the frame determined to be the failed frame; recommend the rescan with the ultrasonic beam to a user in a case where it is determined the rescan with the ultrasonic beam is needed; select an ultrasound image of a measurement frame that serves as a target subjected to measurement from among the ultrasound images of the plurality of frames, based on the feature quantity in a case where it is determined that the rescan with the ultrasonic beam is not needed; and analyze the ultrasound image of the measurement frame to measure a urine volume.

According to the present invention, the ultrasound diagnostic apparatus includes the urinary bladder extraction unit configured to extract a urinary bladder region from each of ultrasound images of a plurality of frames; the feature quantity calculation unit configured to calculate a feature quantity related to the urinary bladder region extracted for each of the ultrasound images of the plurality of frames by the urinary bladder extraction unit; the failed frame determination unit configured to determine whether or not each of the ultrasound images of the plurality of frames is of a failed frame for which the scan with the ultrasonic beam on the subject has failed; the rescan determination unit configured to determine whether or not a rescan with an ultrasonic beam is needed, based on a time-series change in the feature quantity calculated by the feature quantity calculation unit and a time-series position of the ultrasound image of the frame determined to be the failed frame by the failed frame determination unit; the rescan recommendation unit configured to recommend the rescan with the ultrasonic beam to a user in a case where the rescan determination unit determines that the rescan with the ultrasonic beam is needed. Thus, the ultrasound diagnostic apparatus can increase the accuracy of urine volume measurement.

DESCRIPTION OF THE PREFERRED EMBODIMENTS

Embodiments of this invention will be described below with reference to the accompanying drawings.

The description of constituent elements below is given based on representative embodiments of the present invention. However, the present invention is not limited to such embodiments.

In the present specification, a numerical range expressed using "to" means a range including a numerical value preceding "to" as a lower limit value and a numerical value following "to" as an upper limit value.

In the present specification, the terms "identical" and "same" include an error range generally acceptable in the technical field.

First Embodiment

Figure 1:
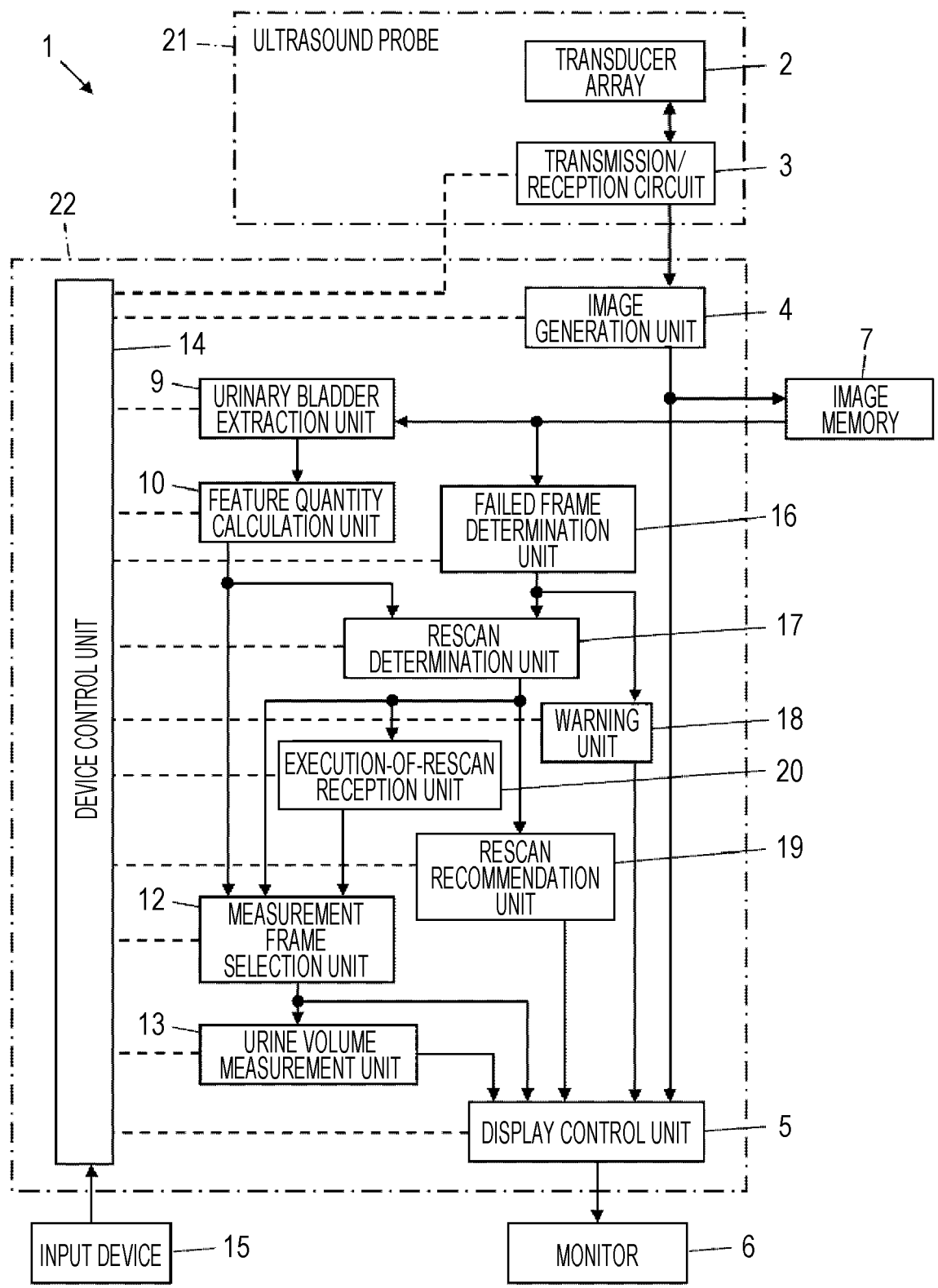
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 includes a transducer array 2. A transmission/reception circuit 3, an image generation unit 4, a display control unit 5, and a monitor 6 are sequentially connected to the transducer array 2. The transducer array 2 and the transmission/reception circuit 3 are included in an ultrasound probe 21. An image memory 7 is connected to the image generation unit 4. A urinary bladder extraction unit 9 and a failed frame determination unit 16 are connected to the image memory 7. A feature quantity calculation unit 10 is connected to the urinary bladder extraction unit 9. A rescan determination unit 17 is connected to the feature quantity calculation unit 10 and the failed frame determination unit 16. A warning unit 18 is connected to the failed frame determination unit 16. A rescan recommendation unit 19 and an execution-of-rescan reception unit 20 are connected to the rescan determination unit 17. A measurement frame selection unit 12 is connected for the feature quantity calculation unit 10, the rescan determination unit 17, and the execution-of-rescan reception unit 20. A urine volume measurement unit 13 is connected to the measurement frame selection unit 12. Each of the measurement frame selection unit 12, the urine volume measurement unit 13, the warning unit 18, and the rescan recommendation unit 19 is connected to the display control unit 5.

A device control unit 14 is connected to the transmission/reception circuit 3, the image generation unit 4, the display control unit 5, the urinary bladder extraction unit 9, the feature quantity calculation unit 10, the measurement frame selection unit 12, the urine volume measurement unit 13, the failed frame determination unit 16, the rescan determination unit 17, the warning unit 18, the rescan recommendation unit 19, and the execution-of-rescan reception unit 20. An input device 15 is connected to the device control unit 14.

The image generation unit 4, the display control unit 5, the urinary bladder extraction unit 9, the feature quantity calculation unit 10, the measurement frame selection unit 12, the urine volume measurement unit 13, the device control unit 14, the failed frame determination unit 16, the rescan determination unit 17, the warning unit 18, the rescan recommendation unit 19, and the execution-of-rescan reception unit 20 constitute a processor 22 for the ultrasound diagnostic apparatus 1.

The transducer array 2 of the ultrasound probe 21 illustrated in FIG. 1 has a plurality of transducers arranged one-dimensionally or two-dimensionally. Each of these transducers transmits an ultrasonic wave in accordance with a drive signal supplied from the transmission/reception circuit 3. Each of these transducers also receives an ultrasonic echo from the subject, and outputs a signal based on the ultrasonic echo. Each of the transducers is configured by forming electrodes at respective ends of a piezoelectric body made of, for example, a piezoelectric ceramic represented by lead zirconate titanate (PZT), a polymer piezoelectric element represented by polyvinylidene difluoride (PVDF), and a piezoelectric single crystal represented by lead magnesium niobate-lead titanate (PMN-PT).

Figure 2:
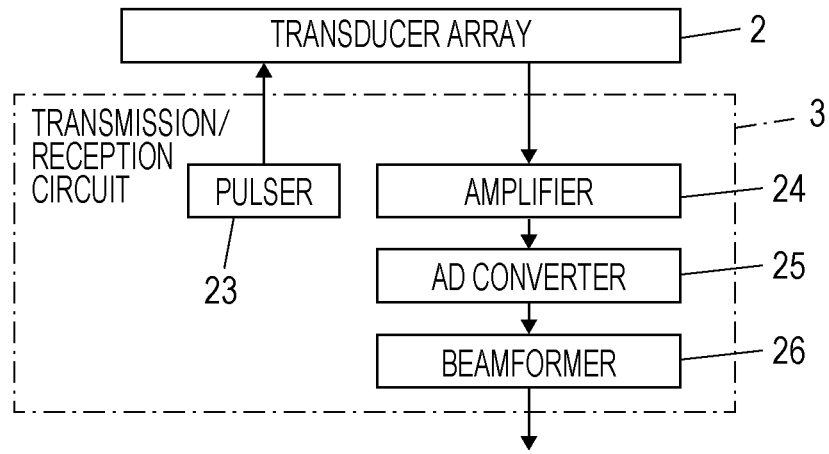
FIG. 2 is a block diagram illustrating an internal configuration of a transmission/reception circuit in the first embodiment of the present invention.

Under the control of the device control unit 14, the transmission/reception circuit 3 transmits ultrasonic waves from the transducer array 2, and generates a sound ray signal based on reception signals acquired by the transducer array 2. As illustrated in FIG. 2, the transmission/reception circuit 3 has a pulser 23 connected to the transducer array 2, and an amplifier 24, an analog-to-digital (AD) converter 25, and a beamformer 26 sequentially connected in series from the transducer array 2.

The pulser 23 includes, for example, a plurality of pulse generators. The pulser 23 adjusts delay amounts of respective drive signals, based on a transmission delay pattern selected in accordance with a control signal from the device control unit 14 so that ultrasonic waves transmitted from the plurality of transducers of the transducer array 2 form an ultrasonic beam, and supplies the resulting drive signals to the respective transducers. As described above, in response to application of a pulsed or continuous-wave voltage to the electrodes of the transducers of the transducer array 2, the piezoelectric body expands and contracts. Consequently, pulsed or continuous-wave ultrasonic waves are generated from the respective transducers, and an ultrasonic beam is formed from a composite wave of those ultrasonic waves.

The transmitted ultrasonic beam is reflected by a target such as a part of a subject, for example, and propagates toward the transducer array 2 of the ultrasound probe 21. An ultrasonic echo propagating toward the transducer array 2 in this manner is received by each of the transducers of the transducer array 2. At this time, in response to receipt of the propagating ultrasonic echo, the transducers of the transducer array 2 expand and contract to generate respective reception signals, which are electric signals, and output these reception signals to the amplifier 24.

The amplifier 24 amplifies a signal input from each of the transducers of the transducer array 2, and transmits the amplified signal to the AD converter 25. The AD converter 25 converts the signals transmitted from the amplifier 24 into pieces of digital reception data, and transmits these pieces of reception data to the beamformer 26. The beamformer 26 performs so-called reception focusing processing in which the pieces of reception data obtained by the AD converter 25 through conversion are given respective delays and then are added in accordance with sonic velocities or a sonic velocity distribution set based on a reception delay pattern selected in accordance with a control signal from the device control unit 14. Through this reception focusing processing, the pieces of reception data obtained by the AD converter 25 through the conversion are subjected to phasing addition, and a sound ray signal to which the focus of the ultrasonic echo converges is acquired.

Figure 3:
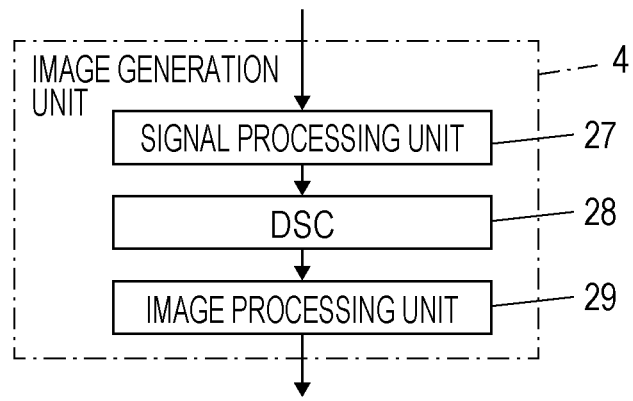
FIG. 3 is a block diagram illustrating an internal configuration of an image generation unit in the first embodiment of the present invention.

As illustrated in FIG. 3, the image generation unit 4 has a configuration in which a signal processing unit 27, a digital scan converter (DSC) 28, and an image processing unit 29 are sequentially connected in series.

In accordance with a depth of a reflected position of the ultrasonic waves, the signal processing unit 27 performs distance-based attenuation correction on the sound ray signal generated by the beamformer 26 of the transmission/reception circuit 3, and then performs envelope detection processing. In this manner, the signal processing unit 27 generates a B-mode image signal, which is tomographic image information related to a tissue in the subject.

The DSC 28 converts (raster-converts) the B-mode image signal generated by the signal processing unit 27 into an image signal according to a normal television signal scanning method.

The image processing unit 29 performs various kinds of necessary image processing such as grayscale processing on the B-mode image signal input from the DSC 28, and then outputs the B-mode image signal to the display control unit 5 and the image memory 7. Hereinafter, the B-mode image signal on which the image processing has been performed by the image processing unit 29 is simply referred to as an ultrasound image.

The image memory 7 is a memory that stores ultrasound images of a series of frames generated by the image generation unit 4 for each diagnosis. The image memory 7 to be used can be a recording medium such as a flash memory, a hard disc drive (HDD), a solid state drive (SDD), a flexible disc (FD), a magneto-optical disc (MO), a magnetic tape (MT), a random access memory (RAM), a compact disc (CD), a digital versatile disc (DVD), a secure digital (SD) card, or a Universal Serial Bus (USB) memory; a server; or the like.

Figure 4:
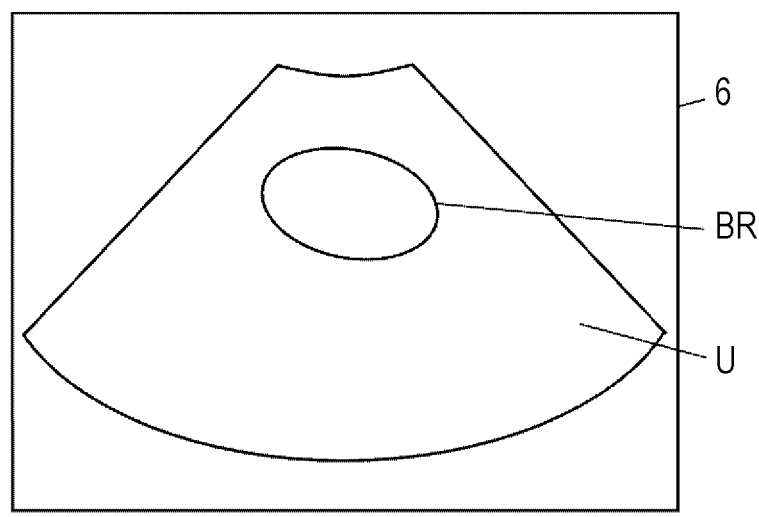
FIG. 4 is a diagram schematically illustrating an example of an ultrasound image including a urinary bladder region in the first embodiment of the present invention.

For example, as illustrated in FIG. 4, the urinary bladder extraction unit 9 extracts a urinary bladder region BR from an ultrasound image U. For example, the urinary bladder extraction unit 9 can use a technique using deep learning described in Krizhevsk et al.: ImageNet Classification with Deep Convolutional Neural Networks, Advances in Neural Information Processing Systems 25, pp. 1106-1114 (2012) to extract the urinary bladder region BR in the ultrasound image U. Alternatively, the urinary bladder extraction unit 9 can use, as another technique, a known technique such as graph cut (Y. Boykov and V. Kolmogorov, "An experimental comparison of min-cut/max-flow algorithm for energy minimization in vision", IEEE Transactions on Pattern Analysis and Machine Intelligence, 26, 9, pp. 1123-1137, 2004), Snakes (A. W. Michael Kass and D. Terzopoulos: "Snakes: Active contour models", Int. J. Computer Vision, 1, 4, pp. 321-331, 1988), or Level Sets (M. Sussman, P. Smereka, and S. Osher: "A level set approach for computing solutions to incompressible two-phase flow", J. Comput. Phys, 114, 1, pp. 146-159, 1994) to extract the urinary bladder region BR.

The feature quantity calculation unit 10 calculates a feature quantity related to the extracted urinary bladder region BR in the ultrasound image U from which the urinary bladder region BR has been extracted by the urinary bladder extraction unit 9. Through image analysis, the feature quantity calculation unit 10 can calculate, as the feature quantity, an area of the extracted urinary bladder region BR, for example. Through image analysis, the feature quantity calculation unit 10 can calculate, as the feature quantity, largest diameters of the urinary bladder region BR in three directions orthogonal to each other, which are used for measuring the volume of the urinary bladder described below, for example. Through image analysis, the feature quantity calculation unit 10 can calculate, as the feature quantity, the largest diameter in any direction of the extracted urinary bladder region BR, the circumferential length of the urinary bladder region BR, or the like, for example.

The failed frame determination unit 16 determines whether or not each of the ultrasound images of the plurality of frames stored in the image memory 7 is an ultrasound image of a failed frame. Herein, the ultrasound image of the failed frame is an ultrasound image of a frame for which a scan with an ultrasonic beam on a subject has failed because there is a portion of the ultrasound probe 21 that is not in contact with the body surface of the subject.

Figure 5:
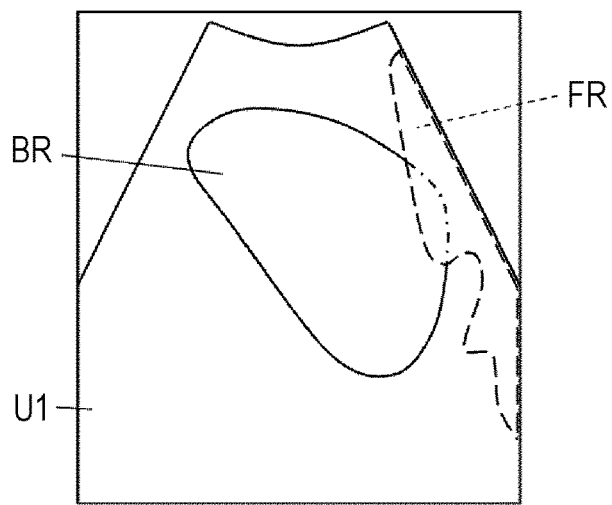
FIG. 5 is a diagram schematically illustrating an example of an ultrasound image of a failed frame.

When there is a portion of the ultrasound probe 21 that is not in contact with the body surface of the subject, a signal having an intensity of a certain level or higher is not obtained. Consequently, a failed region FR filled in black is caused in an ultrasound image U1 as indicated by a region surrounded by a dash line in FIG. 5.

Thus, the failed frame determination unit 16 has, for example, a certain luminance threshold for a luminance value of an ultrasound image. The failed frame determination unit 16 analyzes a luminance profile in a depth direction, for each of the ultrasound images of the plurality of frames stored in the image memory 7. The failed frame determination unit 16 determines a region having a luminance value that is smaller than the luminance threshold to be a failed region FR for which the ultrasound probe 21 is not in contact with the body surface of the subject, and determines an ultrasound image of a frame including the failed region FR to be an ultrasound image of a failed frame.

The warning unit 18 issues a warning to the user if the failed frame determination unit 16 determines that any of the ultrasound images of the plurality of frames stored in the image memory 7 is an ultrasound image of a failed frame. For example, the warning unit 18 can display a message or the like indicating a warning to the user on the monitor 6.

When the image generation unit 4 generates an ultrasound image of a frame including the urinary bladder region BR of the subject, the user usually scans the urinary bladder by changing the position or angle of the ultrasound probe 21 while keeping the ultrasound probe 21 in contact with the body surface of the subject. At this time, the user can scan the urinary bladder by using, for example, a swing method in which the ultrasound probe 21 is inclined on the body surface of the subject while the position of the ultrasound probe 21 is fixed.

Figure 6:
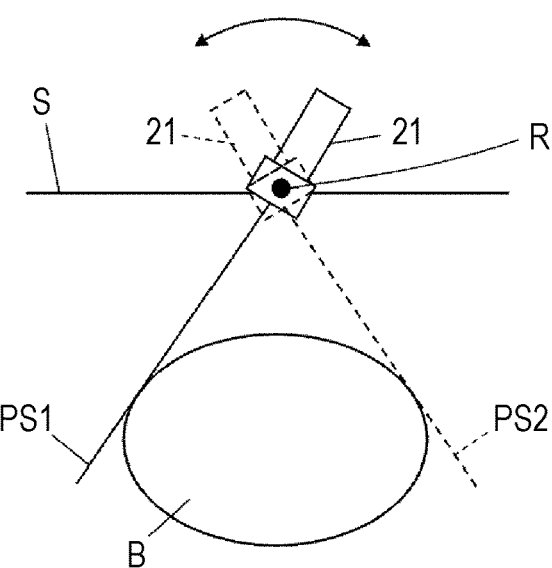
FIG. 6 is a diagram schematically illustrating how a urinary bladder is scanned using a swing method.

When the user scans the urinary bladder using the swing method, the user inclines the ultrasound probe 21 on a body surface S of the subject back and forth between an inclination angle at which a scan cross-section PS1 that passes through one end of a urinary bladder B is imaged and an inclination angle at which a scan cross-section PS2 that passes through the other end of the urinary bladder B with respect to a rotational axis R that is parallel to the arrangement direction of the transducer array 2 as illustrated in FIG. 6, for example.

Figure 7:
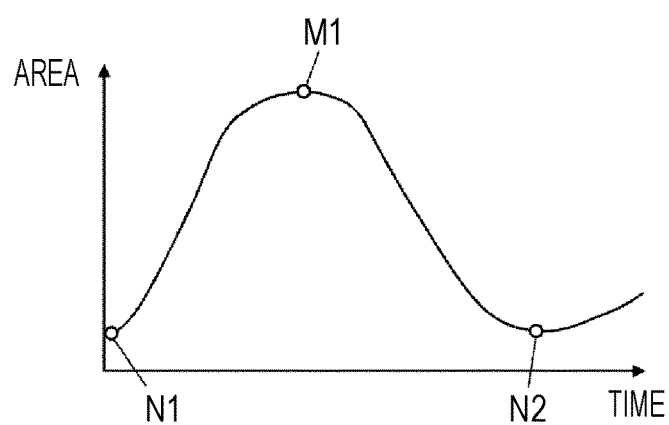
FIG. 7 is a diagram illustrating an example of a temporal change of an area of a urinary bladder region.

At this time, the value of the area of the urinary bladder region BR included in the ultrasound images of the frames consecutively generated by the image generation unit 4 changes in time series such that the value alternately has a local maximum value and a local minimum value as illustrated in FIG. 7, for example. The example of FIG. 7 presents a relationship between the area of the urinary bladder region BR and the generation time of the ultrasound image of the frame for which the area of the urinary bladder region BR is calculated, and the value of the area of the urinary bladder region BR changes in time series to have one local maximum value M1 and two local minimum values N1 and N2. Although the example of FIG. 7 presents the time-series change in the value of the area of the urinary bladder region BR, the largest diameter of the urinary bladder region BR also shows a time-series change as illustrated in FIG. 7.

Figure 8:
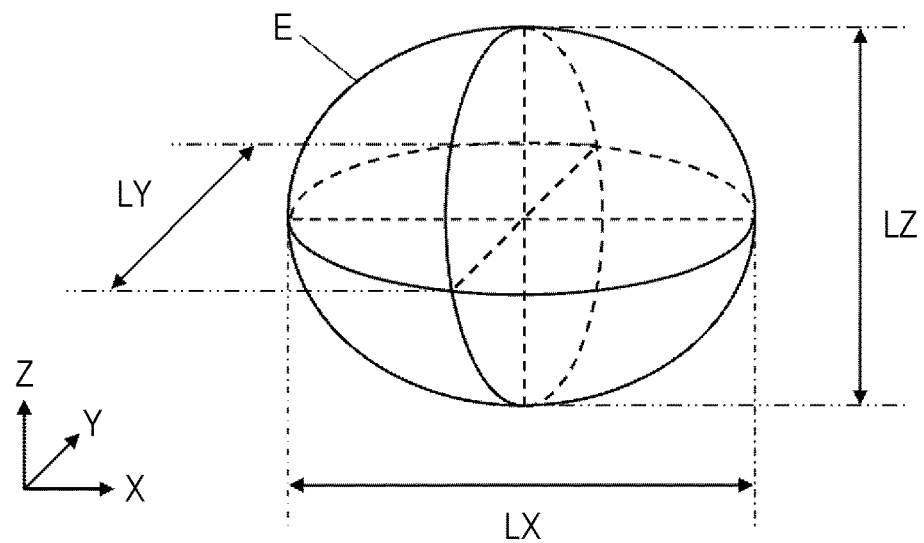
FIG. 8 is a diagram illustrating an example of an ellipsoid.

In general, the urinary bladder B of the subject usually has a substantially ellipsoidal shape. Thus, the urine volume in the urinary bladder B is measured by calculating the volume of the urinary bladder B while the urinary bladder B is regarded as an ellipsoid. As illustrated in FIG. 8, when an ellipsoid E has a symmetrical shape with respect to an XY plane, a YZ plane, and an XZ plane, it is known that the volume of the ellipsoid E is calculated by $(LX \times LY \times LZ) \times \pi/6$, where LX is the largest diameter of the ellipsoid E in the X direction, LY is the largest diameter of the ellipsoid E in the Y direction, LZ is the largest diameter of the ellipsoid E in the Z direction, and a is the circumference ratio. Thus, when the volume of the urinary bladder B is calculated using ultrasound images, it is desirable to perform measurement on ultrasound images of two frames corresponding to scan cross-sections that pass through the center of the urinary bladder B and are orthogonal to each other.

As described above, the ultrasound image of the frame that corresponds to a scan cross-section that pass through the center of the urinary bladder B is an ultrasound image of a frame for which the feature quantities such as the area and the largest diameter of the urinary bladder region BR become a local maximum in the time-series change when a scan with the ultrasonic beam is performed on the urinary bladder B using the swing method, for example.

Figure 9:
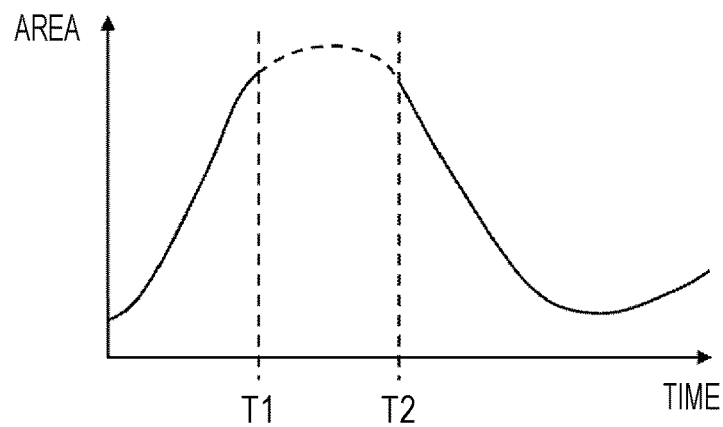
FIG. 9 is a diagram illustrating an example in which the temporal change of the area of the urinary bladder region becomes a local maximum in a section in which the ultrasound image of the failed frame is generated.

The rescan determination unit 17 acquires information representing the time-series change in the feature quantity of the urinary bladder region BR calculated by the feature quantity calculation unit 10 and analyzes this information to estimate whether or not the actual time-series change of the feature quantity becomes a local maximum at the generation time of the ultrasound image of the frame determined to be a failed frame. Based on the estimation result, the rescan determination unit 17 determines whether or not a rescan with an ultrasonic beam is needed. FIG. 9 illustrates a graph presenting a time-series change of the area of the urinary bladder region BR as an example of the information representing the time-series change of the feature quantity of the urinary bladder region BR. In a section from time T1 to time T2, an ultrasound image of a failed frame is generated.

For example, the rescan determination unit 17 analyzes the graph representing a temporal change of the feature quantity to acquire information representing a change of the graph in certain sections before and after the section from the time T1 to the time T2. Based on the acquired information, the rescan determination unit 17 can determine whether or not the feature quantity becomes a local maximum at the generation time of the ultrasound image of the failed frame. For example, when the graph monotonously increases in a certain section immediately before the section from the time T1 to the time T2 and the graph monotonously decreases in a certain section immediately after the section from the time T1 to the time T2, the rescan determination unit 17 can estimate that the feature quantity becomes a local maximum in the section from the time T1 to the time T2. In the rest of the cases, the rescan determination unit 17 can estimate that the feature quantity does not become a local maximum in the section from the time T1 to time T2.

In the example of FIG. 9, the graph monotonously increases the certain section immediately before the section from the time T1 to the time T2 in which the ultrasound image of the failed frame is generated, and the graph monotonously decreases in the certain section immediately after the section from the time T1 to the time T2. Thus, the rescan determination unit 17 estimates that the area of the urinary bladder region BR becomes a local maximum in the section from the time T1 to the time T2.

When the feature quantity is estimated to become a local maximum at the generation time of the failed frame in this manner, the rescan determination unit 17 determines that an ultrasound image of a frame suitable for urine volume measurement is not generated and determines that a rescan with an ultrasonic beam is needed.

Figure 10:
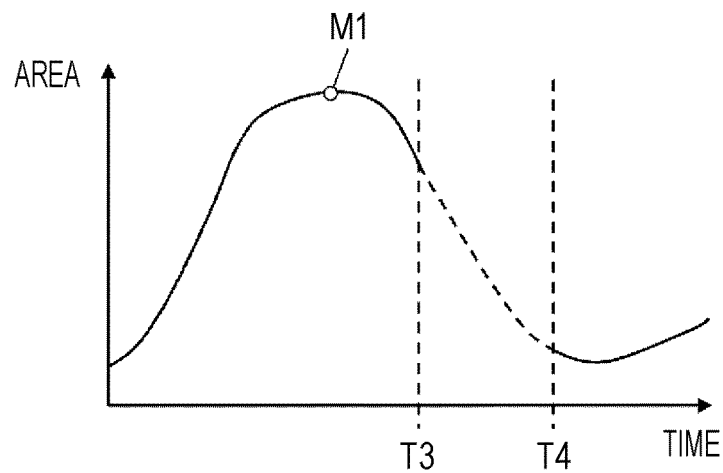
FIG. 10 is a diagram illustrating an example in which the temporal change of the area of the urinary bladder region does not become a local maximum in a section in which the ultrasound image of the failed frame is generated.

For example, in an example illustrated in FIG. 10, the area of the urinary bladder region BR has the local maximum value M1 at a past time relative to a section from a time T3 to a time T4 in which the ultrasound image of the failed frame is generated. In this case, the graph monotonously decreases in a certain section immediately before the section from the time T3 to the time T4 and in a certain section immediately after the section from the time T3 to the time T4. Thus, the rescan determination unit 17 estimates that the area of the urinary bladder region BR does not become a local maximum at the generation time of the ultrasound image of the failed frame.

When the area of the urinary bladder region BR is estimated not to become a local maximum at the generation time of the failed frame in this manner, the rescan determination unit 17 determines that an ultrasound image of a frame suitable for urine volume measurement is generated and determines that a rescan with an ultrasonic beam is not needed.

The input device 15 is a device with which a user performs an input operation, and can include a keyboard, a mouse, a trackball, a touch pad, a touch panel, and the like.

If the rescan determination unit 17 determines that a rescan with an ultrasonic beam is needed, the rescan recommendation unit 19 recommends the rescan with the ultrasonic beam to the user. For example, the rescan recommendation unit 19 can display a message for recommending a rescan with the ultrasonic beam on the monitor 6.

Figure 11:
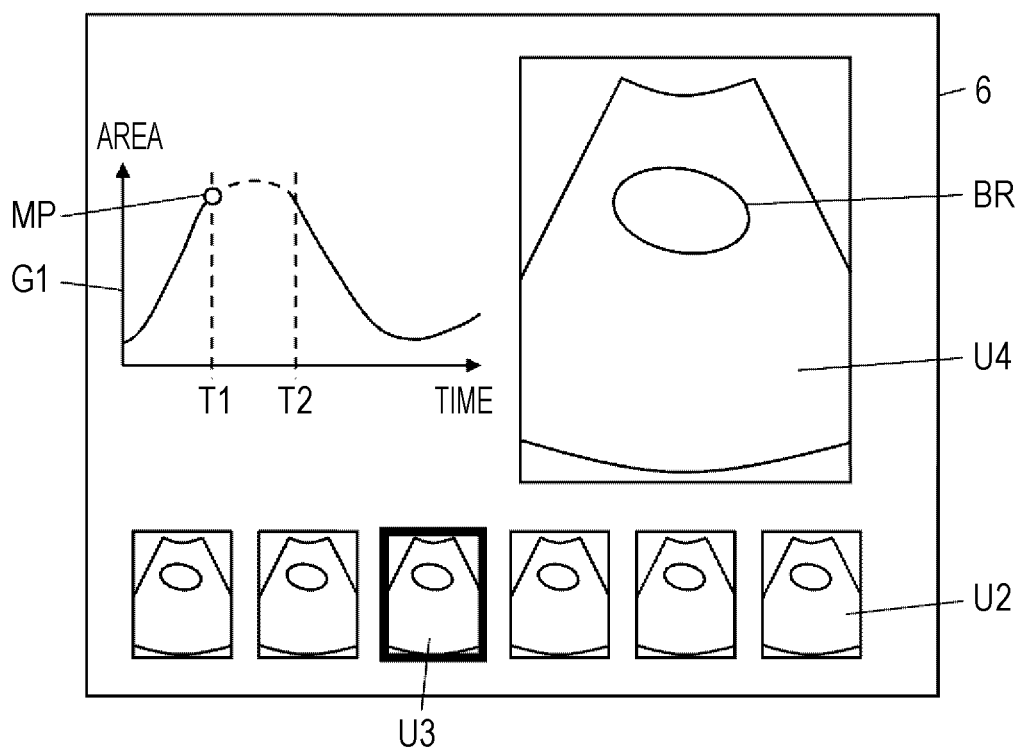
FIG. 11 is a diagram schematically illustrating an example in which a graph representing a time-series change of the area of the urinary bladder region and ultrasound images of a plurality of frames are displayed on a monitor in the first embodiment of the present invention.

For example, the rescan recommendation unit 19 displays, on the monitor 6, a message, a radio button, or the like that prompts the user to select whether or not to perform a rescan with the ultrasonic beam through an input operation via the input device 15. At this time, to make it easier for the user to determine whether or not to perform a rescan with the ultrasonic beam, the rescan recommendation unit 19 can display, on the monitor 6, ultrasound images U2 of a plurality of frames and a graph G1 representing a time-series change of the feature quantity of the urinary bladder region BR corresponding to the ultrasound images U2 of the plurality of frames as illustrated in FIG. 11, for example. In the example of FIG. 11, the ultrasound images U2 of the plurality of frames are displayed to be scrolled in a lower portion of the monitor 6. An ultrasound image U3 of a frame corresponding to a marker MP placed on the graph G1 is selected by the user from among the ultrasound images U2 of the plurality of frames, and an ultrasound image U4 that is the enlarged ultrasound image U3 of this frame is displayed in an upper right portion of the monitor 6 in an enlarged manner.

If the rescan determination unit 17 determines that a rescan with the ultrasonic beam is needed, the execution-of-rescan reception unit 20 receives a selection of whether or not to perform the rescan with the ultrasonic beam in accordance with an input operation performed by the user via the input device 15.

If the execution-of-rescan reception unit 20 receives a selection of not performing the rescan with the ultrasonic beam after the rescan determination unit 17 determines that the rescan with the ultrasonic beam is needed or if the rescan determination unit 17 determines that the rescan with the ultrasonic beam is not needed, the measurement frame selection unit 12 selects an ultrasound image of a measurement frame that serves as a target subjected to measurement from among the ultrasound images of the plurality of frames stored in the image memory 7, based on the feature quantity calculated by the feature quantity calculation unit 10.

If the rescan determination unit 17 determines that the rescan with the ultrasonic beam is not needed, the measurement frame selection unit 12 can acquire the largest feature quantity from among the feature quantities calculated for the ultrasound images of the plurality of frames stored in the image memory 7 by the feature quantity calculation unit 10, and select the ultrasound image of the frame with the largest feature quantity as the ultrasound image of the measurement frame, for example.

If the execution-of-rescan reception unit 20 receives a selection of not performing the rescan with the ultrasonic beam, the measurement frame selection unit 12 can remove an ultrasound image of a frame determined to be the ultrasound image of the failed frame by the failed frame determination unit 16, for example, from the ultrasound images of the plurality of frames stored in the image memory 7, acquire the largest feature quantity among the feature quantities of the ultrasound images of the rest of the frames, and select the ultrasound image of the frame with the largest feature quantity as the ultrasound image of the measurement frame.

The urine volume measurement unit 13 calculates the volume of the urinary bladder B of the subject based on the ultrasound image of the measurement frame selected by the measurement frame selection unit 12 to measure the urine volume in the urinary bladder B. For example, when ultrasound images of two measurement frames corresponding to scan cross-sections that pass through the center of the urinary bladder B and are orthogonal to each other are selected by the measurement frame selection unit 12, the urine volume measurement unit 13 measures lengths of the urinary bladder region BR in the ultrasound images of the two measurement frames, acquires the largest diameters LX, LY, and LZ in the three directions orthogonal to each other, and calculates $(LX \times LY \times LZ) \times \pi/6$. In this manner, the urine volume measurement unit 13 can calculate the volume of the urinary bladder B of the subject.

Under the control of the device control unit 14, the display control unit 5 performs predetermined processing on the ultrasound images of the frames stored in the image memory 7, information representing a warning given by the warning unit 18 to the user, information representing a message for recommending a rescan with the ultrasonic beam output by the rescan recommendation unit 19, information representing the value of the urine volume in the urinary bladder B of the subject measured by the urine volume measurement unit 13 and displays the images and information on the monitor 6.

Under the control of the display control unit 5, the monitor 6 performs various displays. The monitor 6 includes a display device such as a liquid crystal display (LCD) or an organic electroluminescence (EL) display, for example.

The device control unit 14 controls each unit of the ultrasound diagnostic apparatus 1, based on a control program or the like stored in advance.

The processor 22 having the image generation unit 4, the display control unit 5, the urinary bladder extraction unit 9, the feature quantity calculation unit 10, the measurement frame selection unit 12, the urine volume measurement unit 13, the device control unit 14, the failed frame determination unit 16, the rescan determination unit 17, the warning unit 18, the rescan recommendation unit 19, and the execution-of-rescan reception unit 20 may be constituted by a central processing unit (CPU) and a control program for causing the CPU to perform various processes. However, the processor 22 may be constituted using a field programmable gate array (FPGA), a digital signal processor (DSP), an application specific integrated circuit (ASIC), a graphics processing unit (GPU), or another integrated circuit (IC), or any combination thereof.

The image generation unit 4, the display control unit 5, the urinary bladder extraction unit 9, the feature quantity calculation unit 10, the measurement frame selection unit 12, the urine volume measurement unit 13, the device control unit 14, the failed frame determination unit 16, the rescan determination unit 17, the warning unit 18, the rescan recommendation unit 19, and the execution-of-rescan reception unit 20 of the processor 22 may be partially or entirely integrated into a single CPU or the like.

An operation of the ultrasound diagnostic apparatus 1 according to the first embodiment will be described in detail below with reference to a flowchart illustrated in FIG. 12.

First, in step S1, an ultrasound image is generated with the ultrasound probe 21 being kept in contact with the body surface S of the subject by the user, and the generated ultrasound image is displayed on the monitor 6. At this time, an ultrasonic beam is transmitted from the plurality of transducers of the transducer array 2 into the subject in accordance with drive signals from the pulser 23 of the transmission/reception circuit 3. The transducers receive an ultrasound echo from the subject, generates respective reception signals, and output the reception signals to the amplifier 24 of the transmission/reception circuit 3. The reception signals are amplified by the amplifier 24, are subjected to AD conversion by the AD converter 25, and are then subjected to phasing addition by the beamformer 26, so that a sound ray signal is generated. In the image generation unit 4, this sound ray signal is subjected to envelope detection processing by the signal processing unit 27 to be a B-mode image signal, and the B-mode image signal is output to the display control unit 5 through the DSC 28 and the image processing unit 29. Consequently, the ultrasound image U is displayed on the monitor 6 under the control of the display control unit 5 as illustrated in FIG. 4.

At this time, the user adjusts the position or the inclination of the ultrasound probe 21 while checking the ultrasound image U displayed on the monitor 6 so that the urinary bladder region BR of the subject is depicted in the ultrasound image U.

Next, in step S2, it is determined whether or not a measurement mode for measuring the urine volume in the urinary bladder B of the subject is started. For example, when an instruction for starting the measurement mode is given by the user via the input device 15, it is determined that the measurement mode is started. When an instruction for starting the measurement mode is not given by the user, it is determined that the measurement mode is not started. If it is determined that the measurement mode is not started, the process returns to step S1, in which an ultrasound image is generated and displayed. If it is determined that the measurement mode is started in response to the user giving an instruction for starting the measurement mode after adjusting the position of the ultrasound probe 21, the process proceeds to step S3.

If it is determined in step S2 that the measurement mode is started, an ultrasound image is generated as in step S1 and the generated ultrasound image is stored in the image memory 7 in step S3. For example, the user performs a scan with the ultrasonic beam on the urinary bladder B using the swing method in which the urinary bladder B of the subject is imaged while an inclination of the ultrasound probe 21 is changed.

In subsequent step S4, it is determined whether or not the scan with the ultrasonic beam on the urinary bladder B is ended. For example, when an instruction for ending the scan with the ultrasonic beam is given by the user via the input device 15, it is determined that the scan with the ultrasonic beam is ended. When an instruction for ending the scan with the ultrasonic beam is not given by the user, it is determined that the scan with the ultrasonic beam continues. If it is determined that the scan with the ultrasonic beam continues, the process returns to step S3, in which an ultrasound image is generated and stored. In this manner, steps S3 and S4 are repeated while the scan with the ultrasonic beam continues. Consequently, ultrasound images of a series of frames are stored in the image memory 7. If it is determined that the scan with the ultrasonic beam is ended, the process proceeds to step S5.

When there is a portion of the ultrasound probe 21 that is not in contact with the body surface S of the subject when an ultrasound image is generated in step S3, a signal having an intensity of a certain level or higher is not obtained. Consequently, a failed region FR filled in black is caused in an ultrasound image U1 as indicated by a region surrounded by a dash line in FIG. 5, for example.

Thus, in step S5, it is determined whether or not the ultrasound images of the series of frames stored in the image memory 7 include an ultrasound image of a failed frame. At this time, the failed frame determination unit 16 acquires, for each of the ultrasound images of the plurality of frames stored in the image memory 7, a luminance profile in the depth direction and analyzes the acquired luminance profile to recognize a region having a luminance value smaller than a certain luminance threshold value in the ultrasound image to be the failed region FR and determines that the ultrasound image of the frame including the failed region FR to be the ultrasound image of the failed frame. If it is determined that the ultrasound images of the plurality of frames stored in the image memory 7 include an ultrasound image of a failed frame, the process proceeds to step S6.

In step S6, the warning unit 18 warns the user that the ultrasound images of the plurality of frames stored in the image memory 7 include an ultrasound image of a failed frame. For example, the warning unit 18 displays the warning to the user on the monitor 6. This can allow the user to grasp that an ultrasound image of a failed frame is generated and call the user's attention to keeping the ultrasound probe 21 sufficiently in contact with the body surface S of the subject when a rescan with the ultrasonic beam is performed.

In response to the completion of the processing of step S6 in this manner, the process proceeds to step S7.

If it is determined in step S5 that the ultrasound images of the plurality of frames stored in the image memory 7 do not include an ultrasound image of a failed frame, the process proceeds to step S7 by skipping step S6.

In step S7, the urinary bladder extraction unit 9 performs image analysis on each of the ultrasound images of the plurality of frames stored in the image memory 7, and extracts the urinary bladder region BR representing the urinary bladder B of the subject. Information of the extracted urinary bladder region BR and the ultrasound images of the plurality of frames are sent to the feature quantity calculation unit 10.

In step S8, based on the urinary bladder region BR extracted in step S7 from each of the ultrasound images of the plurality of frames, the feature quantity calculation unit 10 calculates, as the feature quantity related to the urinary bladder region BR, the area of the urinary bladder region BR. Since the user has performed the scan with the ultrasonic beam using the swing method in step S3, the area of the urinary bladder region BR calculated in step S6 changes in time series as illustrated in FIG. 7, for example. The information of the calculated area of the urinary bladder region BR and the ultrasound images of the plurality of frames are transmitted to the rescan determination unit 17 and the measurement frame selection unit 12.

In step S9, the rescan determination unit 17 determines whether or not a rescan with the ultrasonic beam is needed, based on a time-series position of the ultrasonic beam of the frame determined to be the ultrasound image of the failed frame in step S5 and the time-series change of the area of the urinary bladder region BR calculated in step S8.

At this time, the rescan determination unit 17 removes the ultrasound image of the frame determined to be the failed frame in step S5, for example, from the ultrasound images of the series of frames stored in the image memory 7 and acquires a graph representing the time-series change of the area of the urinary bladder region BR in the ultrasound images of the rest of the frames.

The urine volume in the urinary bladder B is measured by calculating the volume of the urinary bladder B while regarding the urinary bladder B to be the ellipsoid E. Thus, ultrasound images of frames corresponding to the scan cross-sections that pass through the center of the urinary bladder B are desirably used as the ultrasound images of the frames used in urine volume measurement. The ultrasound images of such frames are ultrasound images of frames in which the area of the urinary bladder region BR becomes a local maximum in the time-series change illustrated in FIG. 7.

Thus, the rescan determination unit 17 analyzes the graph representing the time-series change of the area of the urinary bladder region BR and estimates whether or not the actual area of the urinary bladder region BR has the local maximum value in a time-series section in which the ultrasound image of the failed frame is generated. In this manner, the rescan determination unit 17 can determine whether or not a rescan with the ultrasonic beam is needed.

For example, if the ultrasound image of the failed frame is generated in the section from the time T1 to the time T2 as illustrated in FIG. 9, the rescan determination unit 17 acquires information representing the change in the graph in certain sections before and after the section from the time T1 to the time T2. Based on the acquired information, the rescan determination unit 17 can estimate whether or not the actual area of the urinary bladder region BR has the local maximum value in the section from the time T1 to the time T2.

In the example of FIG. 9, the graph monotonously increases in the certain section immediately before the section from the time T1 to the time T2, and the graph monotonously decreases in the certain section immediately after the section from the time T1 to the time T2. Thus, the rescan determination unit 17 estimates that the actual area of the urinary bladder region BR becomes a local maximum in the section from the time T1 to the time T2, determines that the ultrasound image of the frame suitable for urine volume measurement is not generated, and determines that a rescan with the ultrasonic beam is needed.

In the cases other than the case where the graph monotonously increases in the certain section immediately before the section in which the ultrasound image of the failed frame is generated and the graph monotonously decreases in the certain section immediately after the section in which the ultrasound image of the failed frame is generated in the graph representing the time-series change of the area of the urinary bladder region BR, the rescan determination unit 17 estimates that the actual area of the urinary bladder region BR does not become a local maximum in the section in which the ultrasound image of the failed frame is generated, determines that the ultrasound image of the frame suitable for urine volume measurement is generated, and determines that a rescan with the ultrasonic beam is not needed.

In the example of FIG. 10, the ultrasound image of the failed frame is generated in the section from the time T3 to the time T4 not including the local maximum value M1 and the graph monotonously decreases in a certain section immediately before the section from the time T3 to the time T4 and in a certain section immediately after the section from the time T3 to the time T4. Thus, the rescan determination unit 17 estimates that the actual area of the urinary bladder region BR does not become a local maximum in the section from the time T3 to the time T4.

In step S9, the rescan determination unit 17 determines whether or not a rescan with the ultrasonic beam is needed in this manner. If the rescan determination unit 17 determines that a rescan with the ultrasonic beam is needed, the process proceeds to step S10.

In step S10, the rescan recommendation unit 19 recommends the rescan with the ultrasonic beam to the user, for example, by displaying a message for recommending the rescan with the ultrasonic beam on the monitor 6. Although not illustrated, the rescan recommendation unit 19 displays, on the monitor 6, a message, a radio button, and the like that allows the user to select whether or not to perform a rescan with the ultrasonic beam through an input operation via the input device 15, for example.

At this time, to make it easier for the user to determine whether or not to perform a rescan with the ultrasonic beam, the rescan recommendation unit 19 can display, on the monitor 6, the ultrasound images U2 of the plurality of frames and the graph G1 representing the time-series change of the feature quantity of the urinary bladder region BR corresponding to the ultrasound images U2 of the plurality of frames as illustrated in FIG. 11, for example. In the example of FIG. 11, the ultrasound images U2 of the plurality of frames are displayed to be scrolled in the lower portion of the monitor 6. The ultrasound image U3 of the frame corresponding to the marker MP placed on the graph G1 is selected by the user from among the ultrasound images U2 of the plurality of frames, and the ultrasound image U4 that is the enlarged ultrasound image U3 of this frame is displayed in the upper right portion of the monitor 6 in an enlarged manner.

The user checks the message, the radio button, and the like displayed on the monitor 6 in step S10 and inputs whether or not to perform a rescan with the ultrasonic beam via the input device 15. Then, in step S11, the execution-of-rescan reception unit 20 receives the selection of whether or not to perform the rescan with the ultrasonic beam in response to the input operation performed by the user via the input device 15. For example, in response to the user inputting an instruction for performing a rescan with the ultrasonic beam via the input device 15, the execution-of-rescan reception unit 20 receives a selection for performing the rescan with the ultrasonic beam. In response to the user inputting an instruction for not performing a rescan with the ultrasonic beam via the input device 15, the execution-of-rescan reception unit 20 receives a selection for not performing the rescan with the ultrasonic beam.

In response to the selection for performing the rescan with the ultrasonic beam in step S11, the process returns to step S3 in which the rescan with the ultrasonic beam is started. The processing of steps S3 to S11 is repeated as long as it is determined in step S9 that a rescan with the ultrasonic beam is needed and a selection for performing the rescan with the ultrasonic beam is made in step S11 in this manner.

If it is automatically determined whether or not a rescan with the ultrasonic beam is needed and it is determined that the rescan with the ultrasonic beam is needed in step S9, the rescan with the ultrasonic beam is recommended to the user in step S10 and whether or not to perform the rescan with the ultrasonic beam is selected in step S11 in accordance with the input operation performed by the user. Thus, it is more likely that an ultrasound image of a frame suitable for urine volume measurement is acquired through the rescan with the ultrasonic beam, and the accuracy of urine volume measurement can be increased.

Since whether or not to perform the rescan with the ultrasonic beam is selected in step S11 in accordance with the input operation performed by the user, urine volume measurement can be performed even if the ultrasound probe 21 is partially separated from the body surface S of the subject inevitably because of the body shape or the like of the subject.

In response to the selection for not performing the rescan with the ultrasonic beam in step S11, the process proceeds to step S12.

If it is determined in step S9 that a rescan with the ultrasonic beam is not needed, the process proceeds to step S12 by skipping steps S10 and S11.

In step S12, based on the area of the urinary bladder region BR calculated in step S8, the measurement frame selection unit 12 selects an ultrasound image of a measurement frame that is a target subjected to measurement from among the ultrasound images of the plurality of frames stored in the image memory 7.

For example, if it is determined in step S9 that the rescan with the ultrasonic beam is not needed, the measurement frame selection unit 12 acquires the largest area among the areas of the urinary bladder region BR calculated in step S8 and selects the ultrasound image of the frame with the largest area of the urinary bladder region BR as the ultrasound image of the measurement frame.

For example, if it is determined in step S9 that a rescan with the ultrasonic beam is needed and a selection for not performing the rescan with the ultrasonic beam is made in step S11, the measurement frame selection unit 12 removes the ultrasound image of the frame determined to be the failed frame in step S5 from the ultrasound images of the plurality of frames stored in the image memory 7, acquires the largest area among the areas of the urinary bladder region BR calculated for the ultrasound images of the rest of the frames, and selects the ultrasound image of the frame with the largest area of the urinary bladder region BR as the ultrasound image of the measurement frame.

In response to the ultrasound image of the measurement frame being selected in step S12 in this manner, the process proceeds to step S13.

In step S13, it is determined whether or not ultrasound images of two measurement frames corresponding to two scan cross-sections of the urinary bladder B of the subject orthogonal to each other is selected in step S12 in order to measure the urine volume in the urinary bladder B. In step S12 that has already been completed, only an ultrasound image of the measurement frame corresponding to one of the two scan cross-sections of the urinary bladder B orthogonal to each other has been acquired. Thus, it is determined that the ultrasound images of the two measurement frames corresponding to the two scan cross-sections of the urinary bladder B of the subject orthogonal to each other are not selected, the process returns to step S3, in which the scan with the ultrasonic beam is resumed. At this time, the user rotates the orientation of the ultrasound probe 21 by 90 degrees and performs the scan with the ultrasonic beam.

In steps S3 and S4, an ultrasound image is repeatedly generated and stored unless the user gives an instruction for ending the scan with the ultrasonic beam. In response to the user giving the instruction for ending the scan with the ultrasonic beam in step S4, the process proceeds to step S5. Description of the subsequent processing of steps S5 to S12 is omitted since the details thereof are identical to those already described.

In response to the ultrasound image of the measurement frame being selected in step S12, the process proceeds to step S13.

In step S13, it is determined whether or not the ultrasound images of the two measurement frames corresponding to the two scan cross-sections of the urinary bladder B of the subject orthogonal to each other are selected in step S12. In step S12 performed for the second time, the ultrasound image of the second measurement frame is selected. Thus, it is determined that the ultrasound images of the two measurement frames corresponding to the two scan cross-sections of the urinary bladder B of the subject orthogonal to each other are selected, and the process proceeds to step S14.

Figure 13:
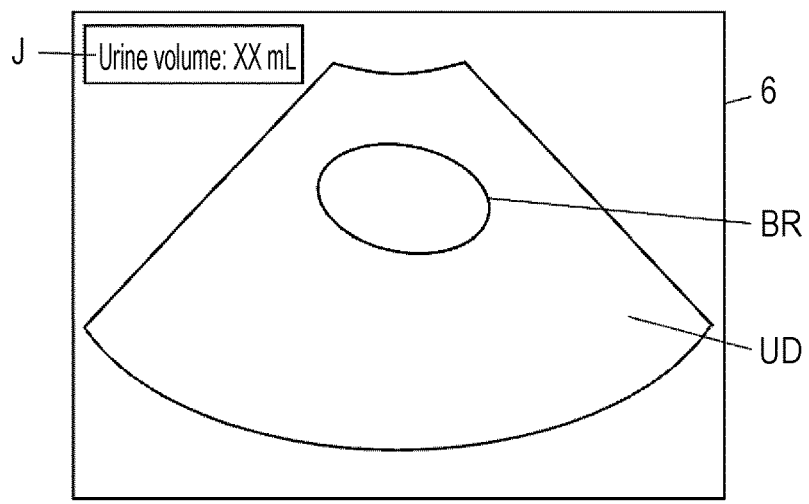
FIG. 13 is a diagram schematically illustrating an example in which a urine volume in a urinary bladder of a subject is displayed on a monitor in the first embodiment of the present invention.

In step S14, the urine volume measurement unit 13 extracts the urinary bladder regions BR from the respective ultrasound images of the two measurement frames selected by the user in step S12 performed twice and calculates the volume of the urinary bladder B of the subject based on the diameters of the extracted urinary bladder region BR to measure the urine volume in the urinary bladder B. For example, the urine volume measurement unit 13 regards the urinary bladder B as the ellipsoid E as illustrated in FIG. 8, measures the largest diameters LX, LY, and LZ of the ellipsoid E respectively in the X, Y, and Z directions from the ultrasound images of the two measurement frames selected by the user in step S12, and calculates (LX×LY×LZ)×π/6. In this manner, the urine volume measurement unit 13 can calculate the volume of the ellipsoid E as the volume of the urinary bladder B. For example, as illustrated in FIG. 13, the urine volume measurement unit 13 displays a measured urine volume J in the urinary bladder B on the monitor 6. In the example of FIG. 13, the ultrasound image UD of the measurement frame selected by the user in the step S12 performed for the second time and the urine volume J in the urinary bladder B are displayed together on the monitor 6.

Figure 12:
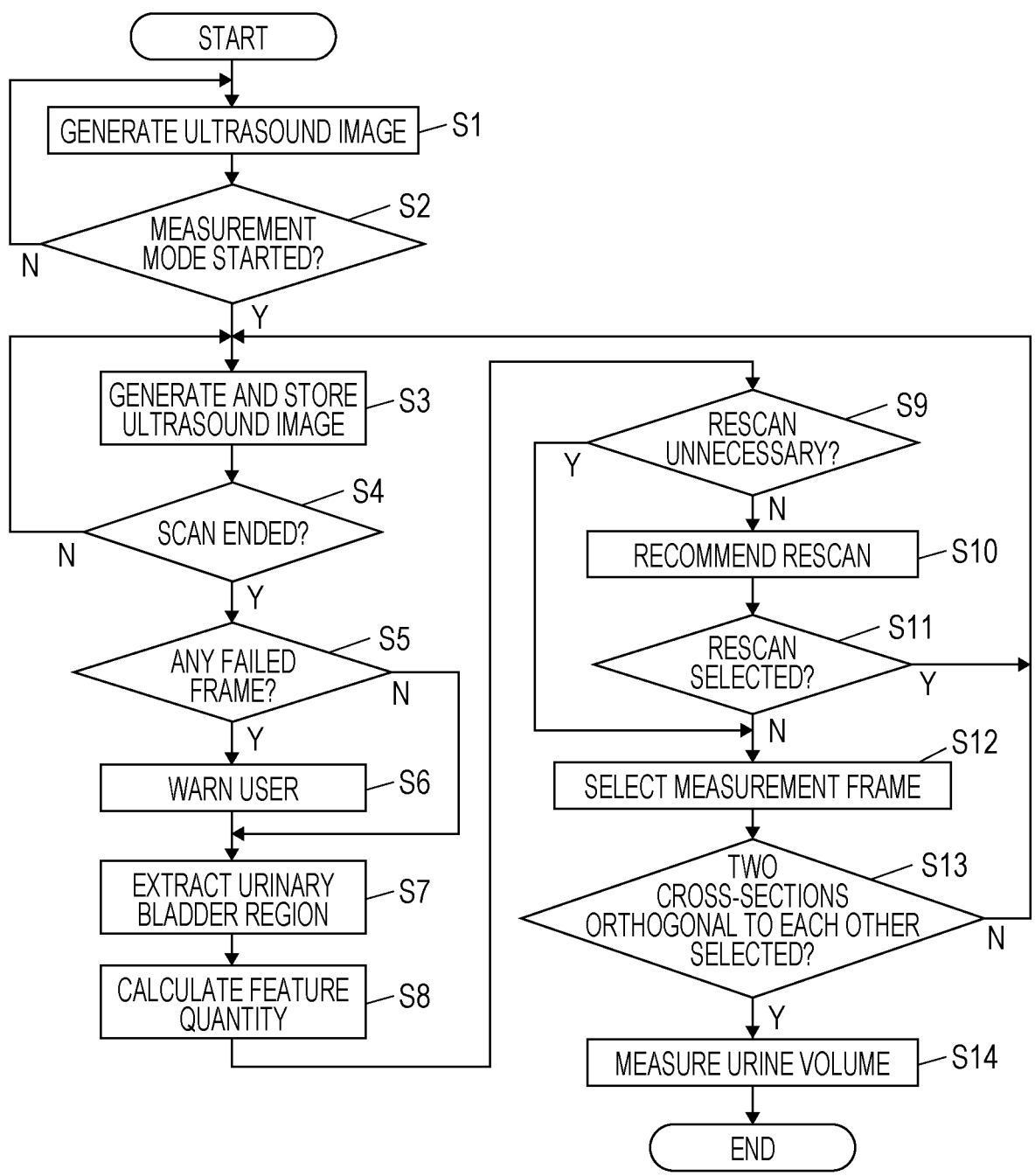
FIG. 12 is a flowchart illustrating an operation of the ultrasound diagnostic apparatus according to the first embodiment of the present invention.

In response to the urine volume in the urinary bladder B of the subject being measured in this manner, the operation of the ultrasound diagnostic apparatus 1 illustrated in the flowchart of FIG. 12 ends.

As described above, the ultrasound diagnostic apparatus 1 according to the first embodiment of the present invention automatically determines in step S5 whether or not the ultrasound images of the plurality of frames include an ultrasound image of a failed frame, determines in step S9 whether or not a rescan with the ultrasonic beam is needed based on this determined result and the feature quantity of the urinary bladder region BR calculated in step S8, and recommends a rescan with the ultrasonic beam to the user if it is determined that the rescan with the ultrasonic beam is needed. Thus, it is more likely that an ultrasound image of a measurement frame suitable for urine volume measurement is acquired through the rescan with the ultrasonic beam, and the accuracy of urine volume measurement can be increased.

The beamformer 26 that performs so-called reception focusing processing is included in the transmission/reception circuit 3. However, the beamformer 26 may be included in the image generation unit 4, for example. Even in this case, as in the case where the beamformer 26 is included in the transmission/reception circuit 3, an ultrasound image is generated by the image generation unit 4.

The image generation unit 4 is included in the processor 22. However, the image generation unit 4 may be included in the ultrasound probe 21.

It is determined in step S4 that the scan with the ultrasonic beam is ended if an instruction for ending the scan with the ultrasonic beam is given by the user. However, it may be determined that the scan with the ultrasonic beam is ended when a predetermined period such as, for example, 15 seconds has elapsed from a timing at which the measurement mode is started in step S2 and the generation and storage of the ultrasound image are started in step S3. In this case, the user's time of giving an instruction for ending the scan with the ultrasonic beam can be saved.

For example, it may be determined whether or not the ultrasound probe 21 is in contact with the body surface S of the subject, and control may be performed to start and end the scan with the ultrasonic beam in accordance with the determined result. When the ultrasound probe 21 is in contact with the body surface S of the subject, an ultrasound image of a frame corresponding to a scan cross-section of the subject is generated. By contrast, when the ultrasound probe 21 is separate from the subjected to be in a so-called aerial radiation state, an entirely black ultrasound image is usually generated. Thus, for example, by analyzing the generated ultrasound image, it can be determined whether or not the ultrasound probe 21 is in contact with the body surface S of the subject. Accordingly, for example, when it is determined that the ultrasound probe 21 is in contact with the body surface S of the subject, the scan with the ultrasonic beam can be started, and when it is determined that the ultrasound probe 21 is separate from the body surface S of the subject, the scan with the ultrasonic beam can be ended. In this case, the user's time of giving an instruction for ending the scan with the ultrasonic beam can be saved.

The above-described plurality of methods for determining the start and end of the scan with the ultrasonic beam can be appropriately combined with each other.

An example in which the user scans the urinary bladder B using the swing method has been described. Alternatively, a slide method in which the ultrasound probe 21 is translated on the body surface S of the subject while keeping the inclination angle of the ultrasound probe 21 constant can also be used for the scan with the ultrasonic beam.

Figure 14:
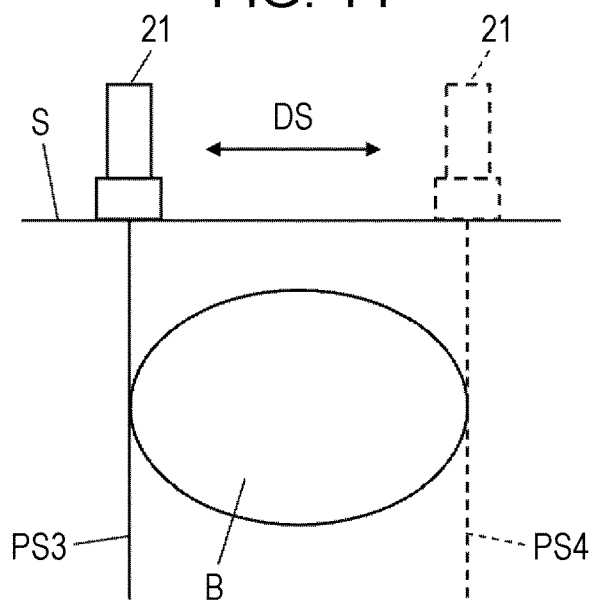
FIG. 14 is a diagram schematically illustrating how the urinary bladder is scanned using a slide method.

For example, as illustrated in FIG. 14, when the user scans the urinary bladder B using the slide method, the user moves the ultrasound probe 21 back and forth between a position at which a scan cross-section PS3 that passes through one end of the urinary bladder B in a sliding direction DS is imaged and a position at which a scan cross-section PS4 that passes through the other end of the urinary bladder B in the sliding direction DS is imaged, where the sliding direction DS is a direction in which the ultrasound probe 21 is translated on the body surface S of the subject.

In this case, the feature quantity such as the area of the urinary bladder region BR in the ultrasound images of the generated frames takes the local minimum values at the position of the ultrasound probe 21 at which the scan cross-sections PS3 is imaged and at the position of the ultrasound probe 21 at which the scan cross-sections PS4 is imaged, and takes the local maximum value at the position of the ultrasound probe 21 at which a scan cross-section that passes through the center of the urinary bladder B is imaged. Thus, as in the case where the scan with the ultrasonic beam is performed using the swing method, the feature quantity of the urinary bladder region BR changes in time series as illustrated in FIG. 7.

Thus, as in the case where the urinary bladder B is scanned using the swing method, even when the urinary bladder B is scanned using the slide method, the rescan determination unit 17 determines whether or not a rescan with the ultrasonic beam is needed based on the feature quantity of the urinary bladder region BR calculated by the feature quantity calculation unit 10 and the time-series position of the ultrasound image of the frame determined to be a failed frame by the failed frame determination unit 16. Thus, it is more likely that the ultrasound image of the measurement frame suitable for urine volume measurement is acquired and the accuracy of urine volume measurement can be increased.

In step S9, the rescan determination unit 17 can acquire the graph representing a time-series change of the feature quantity related to the urinary bladder region BR and perform filtering processing using a so-called smoothing filter or low-pass filter on the curve of the acquired graph to acquire a graph of a smooth curve. Thus, the rescan determination unit 17 analyzes the graph in which an influence of noise is reduced through the filtering processing and can accurately estimate whether or not the actual feature quantity takes the local maximum value at the generation time of the ultrasound image of the failed frame.

In step S10, to make it easier for the user to determine whether or not to perform the rescan with the ultrasonic beam, the rescan recommendation unit 19 displays, on the monitor 6, the ultrasound images U2 of the plurality of frames and the graph G1 representing the time-series change of the feature quantity corresponding to the ultrasound images U2 of the plurality of frames as illustrated in FIG. 11. However, at this time, for example, the ultrasound image of the failed frame may be displayed, on the monitor 6, in a display style different from a display style of the ultrasound images of the normal frames, such as displaying the ultrasound image of the failed frame with a red frame or a thick frame. Thus, the user can clearly grasp the ultrasound image of the failed frame among the ultrasound images of the plurality of frames displayed on the monitor 6 and to select whether or not to perform a rescan with the ultrasonic beam.

The operation of the ultrasound diagnostic apparatus 1 returns to step S3 if it is determined in step S13 that ultrasound images of two measurement frames corresponding to two scan cross-sections of the urinary bladder B of the subject orthogonal to each other are not selected. For example, immediately after step S13, a message prompting rotation of the orientation of the ultrasound probe 21 by 90° may be displayed on the monitor 6. If an instruction regarding an operation to be performed on the ultrasound probe 21 is given to the user in this manner, the user can more smoothly proceed with the procedure of urine volume measurement.

Figure 15:
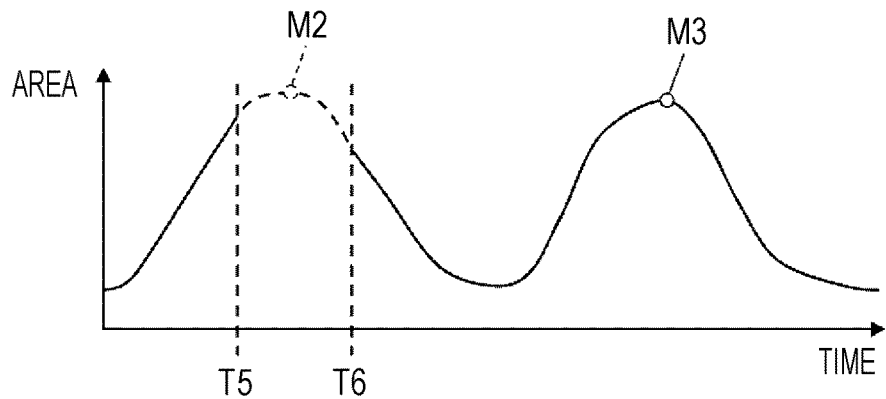
FIG. 15 is a diagram illustrating an example of the time-series change of the area of the urinary bladder region in a plurality of scans with an ultrasonic beam.

When the urinary bladder B is scanned a plurality of times using the swing method or the slide method, the feature quantity of the urinary bladder region BR changes in time series to have a plurality of local maximum values and a plurality of local minimum values such that the local maximum value and the local minimum value alternately repeat. A case is considered where the area of the urinary bladder region BR is supposed to change in time series to have two local maximum values M2 and M3 and an ultrasound image of a failed frame is generated in a section from time T5 to time T6 that includes the local maximum value M2 that is one of the two local maximum values M2 and M3 as illustrated in FIG. 15, for example. In this case, the ultrasound image of the frame having the local maximum value M3 that is the other of the two local maximum values M2 and M3 is correctly generated. Thus, the ultrasound image of this frame can be selected as the ultrasound image UD of the measurement frame.

Thus, for example, the rescan determination unit 17 can perform processing of detecting the local maximum value of the feature quantity in the time-series change of the feature quantity of the urinary bladder region BR and determine whether or not the rescan with the ultrasonic beam is needed based on whether or not the local maximum value of the feature quantity is detected. For example, the rescan determination unit 17 can acquire a graph representing a time-series change of the feature quantity of the urinary bladder region BR, perform processing of detecting the local maximum value of the feature quantity through analysis of the graph, determine that a rescan with the ultrasonic beam is needed if no local maximum value of the feature quantity is detected, and determine that a rescan with the ultrasonic beam is not needed if at least one local maximum value of the feature quantity is detected.

The ultrasound image UD of the measurement frame is desirably an ultrasound image of a frame corresponding to a scan cross-section that passes through the vicinity of the center of the urinary bladder B, that is, an ultrasound image of a frame for which the feature quantity of the urinary bladder region BR becomes the local maximum. Thus, when the feature quantity changes to have a plurality of local maximum values in time series, the ultrasound image UD of the measurement frame is desirably selected from the ultrasound images of the plurality of frames corresponding to the local maximum values of the feature quantity. Thus, for example, the measurement frame selection unit 12 can analyze the graph representing the time-series change of the feature quantity, extract all the local maximum values of the feature quantity, acquire the maximum value among the extracted local maximum values, and select the ultrasound image of the frame corresponding to the acquired maximum value as the ultrasound image UD of the measurement frame.

For example, the measurement frame selection unit 12 can also extract ultrasound images of all frames for which the feature quantity becomes a local maximum in time series as ultrasound images of candidate frames that serve as candidates subjected to measurement, and display the extracted ultrasound images of the candidate frames on the monitor 6 to allow the user to select an ultrasound image of a frame via the input device 15. In this case, for example, the measurement frame selection unit 12 selects, as the ultrasound image UD of the measurement frame, the ultrasound image of the frame selected by the user from among the ultrasound images of the candidate frames displayed on the monitor 6.

As described above, the ultrasound image UD of the measurement frame is selected from among the ultrasound images of the frames for which the feature quantity of the urinary bladder region BR becomes a local maximum, so that it is more likely that the ultrasound image UD of the measurement frame suitable for urine volume measurement is selected and the accuracy of urine volume measurement can be increased.

Second Embodiment

In the first embodiment, the rescan determination unit 17 determines that the feature quantity related to the urinary bladder region BR is not correctly calculated for the ultrasound image of the frame determined to be a failed frame by the failed frame determination unit 16 and determines whether or not a rescan with the ultrasonic beam is needed. However, if the feature quantity is correctly calculated even from the ultrasound image of the frame determined to be a failed frame, it can be determined whether or not a rescan with the ultrasonic beam is needed by taking into account the ultrasound image of this frame.

Figure 16:
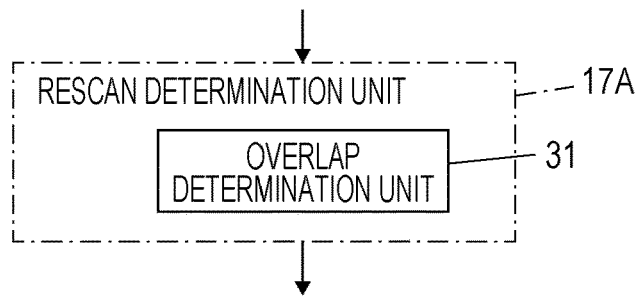
FIG. 16 is a block diagram illustrating an internal configuration of a rescan determination unit in a second embodiment of the present invention.

An ultrasound diagnostic apparatus according to a second embodiment is equivalent to the ultrasound diagnostic apparatus 1 according to the first embodiment illustrated in FIG. 1 that includes a rescan determination unit 17A illustrated in FIG. 16 instead of the rescan determination unit 17. The rescan determination unit 17A includes an overlap determination unit 31.

The overlap determination unit 31 determines whether or not a urinary bladder region BR extracted by the urinary bladder extraction unit 9 and a failed region FR recognized by the failed frame determination unit 16 overlap each other in an ultrasound image of a frame determined to be a failed frame by the failed frame determination unit 16. In the example of the ultrasound image U1 illustrated in FIG. 5, the urinary bladder region BR and the failed region FR overlap each other.

In the ultrasound image U1 of the frame in which the urinary bladder region BR and the failed region FR overlap each other, the presence of an overlapping part of the urinary bladder region BR and the failed region FR makes it difficult to identify the actual urinary bladder region BR and thus to correctly calculate the feature quantity of the urinary bladder region BR. On the other hand, in an ultrasound image of a frame in which the urinary bladder region BR and the failed region FR are separate from each other, since no overlapping part of the urinary bladder region BR and the failed region FR is present, the urinary bladder region BR is identified and thus the feature quantity of the urinary bladder region BR can be correctly calculated.

Thus, the rescan determination unit 17A determines an ultrasound image of a frame in which the overlap determination unit 31 determines that the urinary bladder region BR and the failed region FR overlap each other to be an ultrasound image of a frame for which the feature quantity of the urinary bladder region BR is not correctly calculated, among ultrasound images of frames determined to be failed framed by the failed frame determination unit 16, and removes a value of the feature quantity corresponding to the ultrasound image of this frame from the graph representing the time-series change of the feature quantity. The rescan determination unit 17A determines that the ultrasound image of the frame in which the urinary bladder region BR and the failed region FR are separate from each other is an ultrasound image of a frame for which the feature quantity of the urinary bladder region BR is correctly calculated, and includes the value of the feature quantity corresponding to the ultrasound image of this frame in the graph representing the time-series change of the feature quantity similarly to the values of the feature quantity for the ultrasound images of the normal frames.

The rescan determination unit 17A analyzes the graph representing the time-series change of the feature quantity of the urinary bladder region BR thus acquired to determine whether or not a rescan with the ultrasonic beam is needed. The rescan determination unit 17A determines a rescan with the ultrasonic beam is not needed even if an ultrasound image of a frame for which the feature quantity becomes a local maximum is an ultrasound image of a frame that is determined to be a failed frame but in which the urinary bladder region BR and the failed region FR are separate from each other.

In this case, for example, the measurement frame selection unit 12 acquires the largest feature quantity from among the feature quantities corresponding to the ultrasound image of the failed frame in which the urinary bladder region BR and the failed region FR are separate from each other and to the ultrasound images of the normal frames, and selects the ultrasound image of the frame with the largest feature quantity as the ultrasound image UD of the measurement frame.

As described above, according to the ultrasound diagnostic apparatus of the second embodiment, even if the failure region FR is confirmed in the ultrasound image by the failed frame determination unit 16 but the urinary bladder region BR extracted by the urinary bladder extraction unit 9 is separate from the failed region FR, the rescan determination unit 17A determines that the rescan with the ultrasonic beam is not needed. Thus, a probability of an unnecessary rescan with the ultrasonic beam being performed reduces and the user can proceed with the procedure of urine volume measurement more quickly.

The measurement frame selection unit 12 selects the ultrasound image UD of the measurement frame from among the ultrasound image of the failed frame in which the urinary bladder region BR and the failed region FR are separate from each other and the ultrasound images of the normal frames. Thus, it is more likely that the ultrasound image of the frame suitable for urine volume measurement is selected and the accuracy of urine volume measurement can be increased.

Third Embodiment

In the first embodiment, whether or not each of the ultrasound images of the plurality of frames stored in the image memory 7 is of a failed frame is determined in step S5 after a scan with the ultrasonic beam is determined to be ended in step S4. However, the determination of the failed frame can be performed each time an ultrasound image is generated and stored, and a warning to the user can be given in accordance with the determined result.

Figure 17:
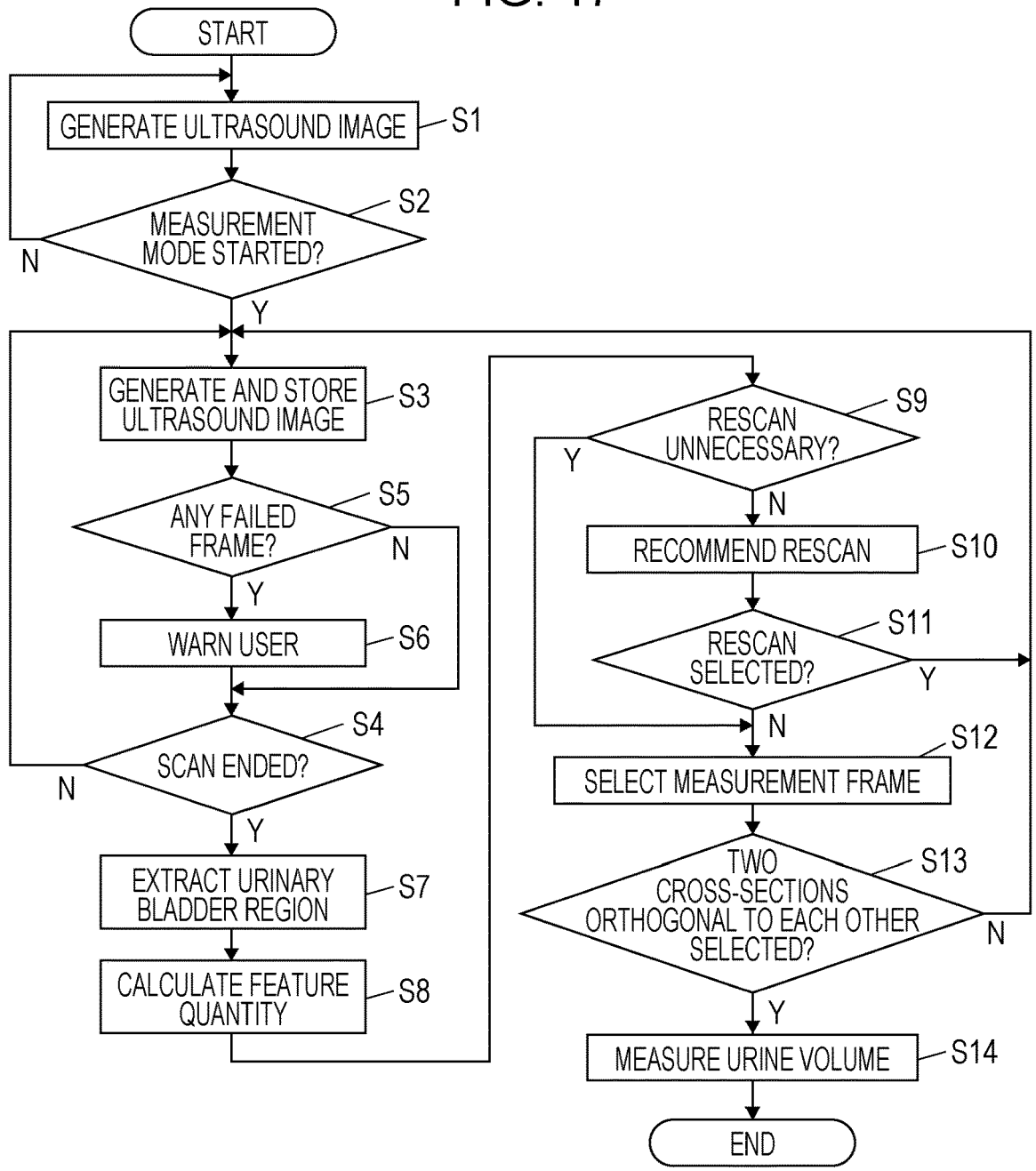
FIG. 17 is a flowchart illustrating an operation of an ultrasound diagnostic apparatus according to a third embodiment of the present invention.

An ultrasound diagnostic apparatus according to a third embodiment is the same as the ultrasound diagnostic apparatus 1 according to the first embodiment illustrated in FIG. 1 but operates in accordance with a flowchart illustrated in FIG. 17. The flowchart of FIG. 17 is equivalent to the flowchart in the first embodiment illustrated in FIG. 12 in which steps S5 and S6 are moved between the steps S3 and S4.

In the third embodiment, in response to an ultrasound image being generated and stored in step S3, the process proceeds to step S5.

In step S5, the failed frame determination unit 16 analyzes an ultrasound image of the latest frame stored in the image memory 7 in step S3 to determine whether or not the ultrasound image of this frame is of a failed frame. In response to the ultrasound image of this frame being determined to be an ultrasound image of a failed frame, the process proceeds to step S6.

In step S6, the warning unit 18 warns the user that the ultrasound image of the failed frame is determined in step S5.

As described above, the ultrasound diagnostic apparatus according to the third embodiment of the present invention performs determination of the failed frame in step S5 each time an ultrasound image is generated and stored in step S3 and warns the user in step S6 if determining that the ultrasound image of that frame is an ultrasound image of a failed frame. Thus, the user performs a scan with the ultrasonic beam while immediately reacting to the warning and carefully keeping the ultrasound probe 21 in contact with the body surface S of the subject. Consequently, many ultrasound images of normal frames can be obtained with the ultrasound probe 21 being kept in contact with the body surface S of the subject. Thus, it is more likely that the ultrasound image UD of the measurement frame suitable for urine volume measurement is selected, and the accuracy of urine volume measurement can be increased.

Figure 18:
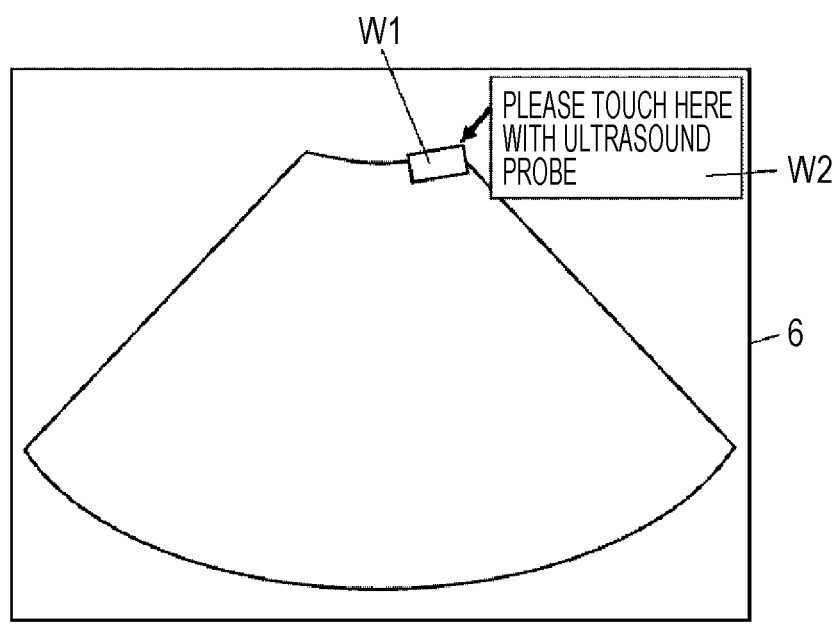
FIG. 18 is a diagram schematically illustrating an example in which a portion of an ultrasound probe that is not in contact with the body surface of a subject is displayed on a monitor in the third embodiment of the present invention.

When the warning unit 18 warns the user in step S6, information indicating a portion of the ultrasound probe 21 that is not in contact with the body surface S of the subject may be displayed on the monitor 6. For example, the failed frame determination unit 16 determines that a shallowest portion in an ultrasound image that is located on a shallow portion side of the failed region FR in the depth direction of the ultrasound image to be a portion of the ultrasound probe 21 that is not in contact with the body surface S of the subject. The user can be notified of the portion of the ultrasound probe 21 that is not in contact with the body surface S of the subject by displaying the portion on the monitor 6 as illustrated in FIG. 18. In the example of FIG. 18, a marker W1 representing the portion of the ultrasound probe 21 that is not in contact with the body surface S of the subject and a message W2 "PLEASE TOUCH HERE WITH ULTRASOUND PROBE" for instructing the user to bring the portion indicated by the marker W1 into contact with the body surface S of the subject are displayed on the monitor 6.

This allows the user to specifically grasp the portion of the ultrasound probe 21 that is not in contact with the body surface S of the subject and can bring the ultrasound probe 21 into contact with the body surface S of the subject.

The processing of steps S7 and S8 may be performed subsequently to step S5 or S6. Consequently, extraction of the urinary bladder region BR and calculation of the feature quantity are sequentially performed on the ultrasound image of the latest frame generated and stored in the image memory 7 in step S3. Thus, as compared with the case where extraction of the urinary bladder region BR and calculation of the feature quantity are performed on the ultrasound images of the plurality of frames stored in the image memory 7 after step S4 in the first embodiment, a waiting time at the time of extraction of the urinary bladder region BR and calculation of the feature quantity can be reduced and urine volume measurement can be performed more quickly.

Description is given such that the configuration of the third embodiment is applied to the ultrasound diagnostic apparatus 1 according to the first embodiment. However, the configuration of the third embodiment is similarly applicable to the ultrasound diagnostic apparatus according to the second embodiment.

Fourth Embodiment

In the first embodiment, the failed frame determination unit 16 determines a failed frame by recognizing the failed region FR based on the luminance profile in the depth direction of the ultrasound image. However, the method for determining the failed frame is not limited to this.

When gas accumulates in the abdomen of the subject and the ultrasound probe 21 is insufficiently pressed against the body surface S of the subject, an ultrasound image of a failed frame that contains the unclear urinary bladder region BR may be generated. In such a case, if the ultrasound probe 21 is pressed further against the body surface S of the subject, the gas moves inside the subject and an ultrasound image clearly depicting the urinary bladder region BR is obtained.

Thus, for example, the ultrasound image of the failed frame can be determined based on an edge clarity of the urinary bladder region BR instead of using the luminance profile in the depth direction of the ultrasound image. The edge clarity of the urinary bladder region BR is an index value, and has a larger value as the outline of the bladder region BR is clear and has a smaller value as the outline of the bladder region BR is unclear.

An ultrasound diagnostic apparatus according to a fourth embodiment is the same as the ultrasound diagnostic apparatus 1 according to the first embodiment illustrated in FIG. 1.

The failed frame determination unit 16 in the fourth embodiment has a predetermined edge clarity threshold for the edge clarity of the urinary bladder region BR, for example. The failed frame determination unit 16 in the fourth embodiment performs image analysis on the ultrasound image of the frame stored in the image memory 7 to calculate the edge clarity of the urinary bladder region BR.

The failed frame determination unit 16 in the fourth embodiment determines that the failed region FR where pressing of the ultrasound probe 21 against the body surface S of the subject is insufficient is confirmed in the ultrasound image if the calculated edge clarity is smaller than the predetermined edge clarity threshold, and determines the ultrasound image of that frame is an ultrasound image of a failed frame.

If the calculated edge clarity is greater than or equal to the predetermined edge clarity threshold, the failed frame determination unit 16 determines that the failed region FR where pressing of the ultrasound probe 21 against the body surface S of the subject is insufficient is not present in the ultrasound image and determines that the ultrasound image of that frame is an ultrasound image of a normal frame.

As described above, similarly to the ultrasound diagnostic apparatus 1 according to the first embodiment, even when the ultrasound image of the failed frame is determined based on the edge clarity of the urinary bladder region BR, whether or not a rescan with the ultrasonic beam is needed is determined based on the determined result obtained by the failed frame determination unit 16 and the feature quantity of the urinary bladder region BR. If it is determined that the rescan with the ultrasonic beam is needed, the rescan with the ultrasonic beam is recommended to the user. Thus, it is more likely that the ultrasound image UD of the measurement frame suitable for urine volume measurement is acquired through the rescan with the ultrasonic beam, and the accuracy of urine volume measurement can be increased.

The configuration of the third embodiment can be combined with the fourth embodiment. In this case, for example, the warning unit 18 has, for the edge clarity of the urinary bladder region BR, an edge clarity warning threshold that is greater than the edge clarity threshold which the failed frame determination unit 16 has. The warning unit 18 can display, on the monitor 6, a warning for pressing the ultrasound probe 21 against the body surface S of the subject harder if the edge clarity of the urinary bladder region BR is smaller than the edge clarity threshold warning threshold. Thus, with reference to the warning displayed on the monitor 6, the user presses the ultrasound probe 21 against the body surface S of the subject and can obtain an ultrasound image of a frame clearly depicting the clear urinary bladder region BR.

Fifth Embodiment

In the fourth embodiment, an ultrasound image of a failed frame is determined based on the edge clarity of the urinary bladder region BR. However, for example, a failed frame can be determined based on a contact pressure of the ultrasound probe 21 when the ultrasound probe 21 is pressed against the body surface S of the subject.

Figure 19:
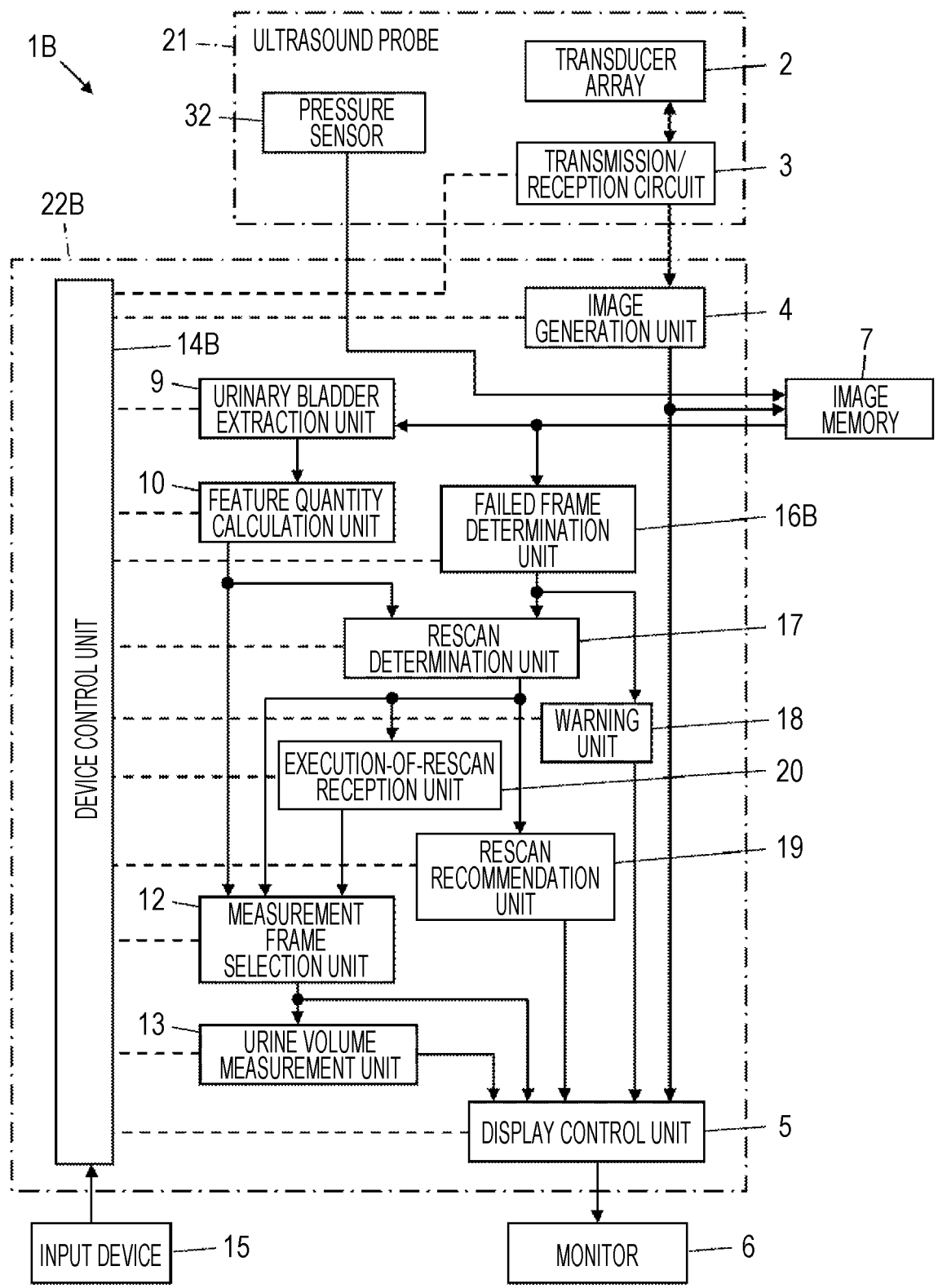
FIG. 19 is a block diagram illustrating a configuration of an ultrasound diagnostic apparatus according to a fifth embodiment of the present invention.

As illustrated in FIG. 19, an ultrasound diagnostic apparatus 1B according to a fifth embodiment is equivalent to the ultrasound diagnostic apparatus 1 according to the first embodiment illustrated in FIG. 1 in which a pressure sensor 32 is attached to the ultrasound probe 21 and that includes a device control unit 14B instead of the device control unit 14, a failed frame determination unit 16B instead of the failed frame determination unit 16, and a processor 22B instead of the processor 22.

The pressure sensor 32 is attached to the ultrasound probe 21 and is connected to the image memory 7. The pressure sensor 32 measures a pressure which the ultrasound probe 21 receives from the body surface S of the subject when the ultrasound probe 21 is pressed against the body surface S of the subject, that is, a contact pressure of the ultrasound probe 21 to the body surface S of the subject. Information on the contact pressure measured by the pressure sensor 32 is sent to the image memory 7, and is stored in the image memory 7 together with an ultrasound image of a frame generated by the image generation unit 4 at the same time.

The failed frame determination unit 16B has a predetermined contact pressure threshold for the contact pressure of the ultrasound probe 21. If the contact pressure measured by the pressure sensor 32 is lower than the predetermined contact pressure threshold, the failed frame determination unit 16B determines that a failed region FR where pressing of the ultrasound probe 21 against the body surface S of the subject is insufficient is confirmed in the ultrasound image of the frame corresponding to the contact pressure, and determines that the ultrasound image of that frame is an ultrasound image of a failed frame.

If the contact pressure measured by the pressure sensor 32 is greater than or equal to the predetermined contact pressure, the failed frame determination unit 16B determines that the failed region FR where pressing of the ultrasound probe 21 against the body surface S of the subject is insufficient is not present in the ultrasound image of the frame corresponding to the contact pressure, and determines that the ultrasound image of that frame is an ultrasound image of a normal frame.

As described above, similarly to the ultrasound diagnostic apparatus 1 according to the first embodiment, even when the ultrasound image of the failed frame is determined based on the contact pressure of the ultrasound probe 21 against the body surface S of the subject, whether or not a rescan with the ultrasonic beam is needed is determined based on the determined result obtained by the failed frame determination unit 16B and the feature quantity of the urinary bladder region BR. If it is determined that the rescan with the ultrasonic beam is needed, the rescan with the ultrasonic beam is recommended to the user. Thus, it is more likely that the ultrasound image UD of the measurement frame suitable for urine volume measurement is acquired through the rescan with the ultrasonic beam, and the accuracy of urine volume measurement can be increased.

The configuration of the third embodiment can be combined with the fifth embodiment. In this case, for example, the warning unit 18 has, for the contact pressure of the ultrasound probe 21 against the body surface S of the subject, a contact pressure warning threshold that is greater than the contact pressure threshold which the failed frame determination unit 16B has. The warning unit 18 can display, on the monitor 6, a warning for pressing the ultrasound probe 21 against the body surface S of the subject harder if the contact pressure measured by the pressure sensor 32 is smaller than the contact pressure warning threshold. Thus, with reference to the warning displayed on the monitor 6, the user presses the ultrasound probe 21 against the body surface S of the subject and can obtain an ultrasound image of a frame clearly depicting the clear urinary bladder region BR.

Sixth Embodiment

The ultrasound diagnostic apparatus 1 according to the first embodiment has a configuration in which the monitor 6, the input device 15, and the ultrasound probe 21 are directly connected to the processor 22. However, for example, the monitor 6, the input device 15, the ultrasound probe 21, and the processor 22 may be connected indirectly to each other via a network.

Figure 20:
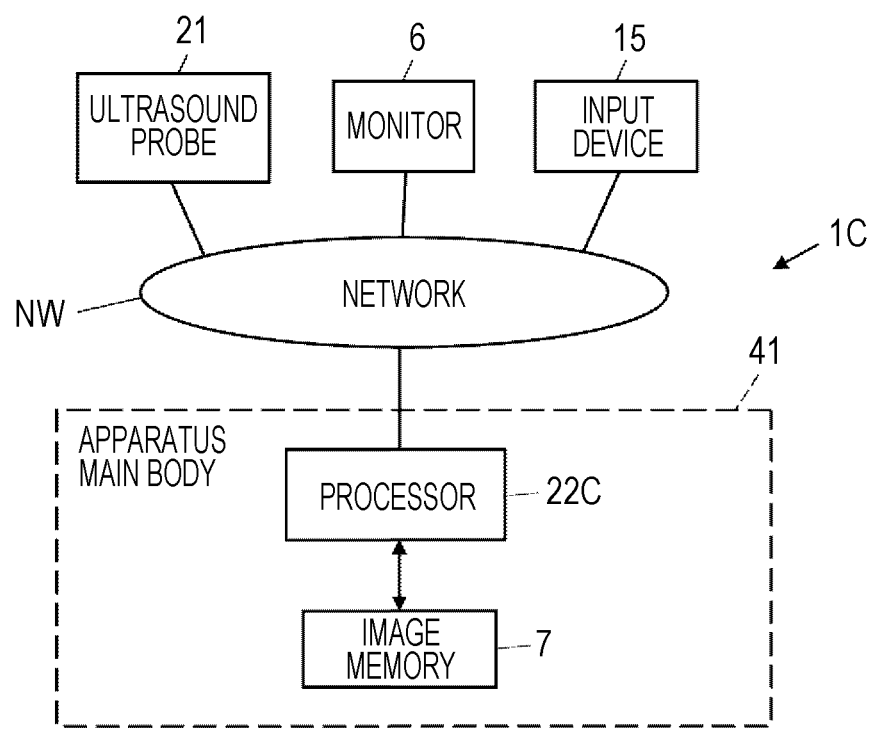
FIG. 20 is a block diagram illustrating a configuration of an ultrasound diagnostic apparatus according to a sixth embodiment of the present invention.

As illustrated in FIG. 20, in an ultrasound diagnostic apparatus 1C according to a sixth embodiment, the monitor 6, the input device 15, and the ultrasound probe 21 are connected to an ultrasound diagnostic apparatus main body 41 via a network NW. The ultrasound diagnostic apparatus main body 41 is equivalent to the ultrasound diagnostic apparatus 1 according to the first embodiment illustrated in FIG. 1 from which the monitor 6, the input device 15, and the ultrasound probe 21 are omitted, and is constituted by the image memory 7 and a processor 22C.

Similarly to the ultrasound diagnostic apparatus 1 according to the first embodiment, even if the ultrasound diagnostic apparatus 1C has such a configuration, whether or not a rescan with the ultrasonic beam is needed is determined based on the determined result obtained by the failed frame determination unit 16 and the feature quantity of the urinary bladder region BR. If it is determined that the rescan with the ultrasonic beam is needed, the rescan with the ultrasonic beam is recommended to the user. Thus, it is more likely that the ultrasound image UD of the measurement frame suitable for urine volume measurement is acquired through the rescan with the ultrasonic beam, and the accuracy of urine volume measurement can be increased.

Since the monitor 6, the input device 15, and the ultrasound probe 21 are connected to the ultrasound diagnostic apparatus main body 41 via the network NW, the ultrasound diagnostic apparatus main body 41 can be used as a so-called remote server. Thus, for example, the user can examine the subject by preparing the monitor 6, the input device 15, and the ultrasound probe 21, so that convenience at the time of ultrasonic diagnosis can be improved.

For example, when a thin portable computer called a tablet is used as the monitor 6 and the input device 15, the user can more easily perform urine volume measurement. Thus, convenience of the urine volume measurement can be further improved.

The monitor 6, the input device 15, and the ultrasound probe 21 are connected to the ultrasound diagnostic apparatus main body 41 via the network NW. At this time, the monitor 6, the input device 15, and the ultrasound probe 21 may be connected to the network NW with cables or wirelessly.

Description is given such that the configuration of the sixth embodiment is applied to the first embodiment. However, the configuration of the sixth embodiment is similarly applied to the second to fifth embodiments.

REFERENCE SIGNS LIST 1, 1B, 1C ultrasound diagnostic apparatus
2 transducer array
3 transmission/reception circuit
4 image generation unit
5 display control unit
6 monitor
7 image memory
9 urinary bladder extraction unit
10 feature quantity calculation unit
12 measurement frame selection unit
13 urine volume measurement unit
14, 14B device control unit
15 input device
16, 16B failed frame determination unit
17, 17A rescan determination unit
18 warning unit
19 rescan recommendation unit
20 execution-of-rescan reception unit
21 ultrasound probe
22, 22B, 22C processor
23 pulser
24 amplifier
25 AD converter
26 beamformer
27 signal processing unit
28 DSC
29 image processing unit
31 overlap determination unit
32 pressure sensor
41 ultrasound diagnostic apparatus main body
B urinary bladder
BR urinary bladder region
C outline
DS sliding direction
E ellipsoid
FR failed region
G1 graph
J urine volume
LX, LY, LZ largest diameter
M1 to M3 local maximum value
MP, W1 marker
N1, N2 local minimum value
PS1, PS2, PS3, PS4 scan cross-section
R rotational axis
S body surface
T1 to T6 time
U, U1 to U4, UD ultrasound image
W2 message

What is claimed is:

1. An ultrasound diagnostic apparatus comprising:
an ultrasound probe;
an input device configured to accept an input operation of a user;
a processor configured to
acquire ultrasound images of a plurality of frames through a scan with an ultrasonic beam on a subject using the ultrasound probe,
extract a urinary bladder region from each of the ultrasound images of the plurality of frames,
calculate a feature quantity related to a size of the urinary bladder region extracted for each of the ultrasound images of the plurality of frames,
determine whether or not each of the ultrasound images of the plurality of frames is of a failed frame for which the scan with the ultrasonic beam on the subject has failed,
determine whether or not a rescan with the ultrasonic beam is needed, based on a time-series change in the feature quantity and a position on a time of the ultrasound image of the frame determined to be the failed frame,
upon determining that the rescan with the ultrasonic beam is needed,
recommend the rescan with the ultrasonic beam to the user,
receive a selection of whether or not to perform the rescan with the ultrasonic beam, in accordance with the input operation performed by the user via the input device,
upon determining that the rescan with the ultrasonic beam is not needed or receiving a selection of not performing the rescan with the ultrasonic beam,
select an ultrasound image of a measurement frame that serves as a target subjected to measurement from among the ultrasound images of the plurality of frames, based on the feature quantity,
analyze the ultrasound image of the measurement frame, and calculate a urine volume in the selected ultrasound image of the measurement frame.

2. The ultrasound diagnostic apparatus according to claim 1,
wherein the processor is further configured to
perform image analysis on each of the ultrasound images of the plurality of frames, and
upon confirming a failed region where the ultrasound probe is not in contact with the subject in the ultrasound image based on a luminance profile in a depth direction of the ultrasound image, determine that the ultrasound image is of a failed frame.

3. The ultrasound diagnostic apparatus according to claim 1, wherein the processor is further configured to perform image analysis on each of the ultrasound images of the plurality of frames, and upon confirming a failed region where the ultrasound probe is not in contact with the subject in the ultrasound image based on a luminance profile in a depth direction of the ultrasound image, determine that the ultrasound image is of a failed frame.

4. The ultrasound diagnostic apparatus according to claim 1,
wherein the processor is further configured to
perform image analysis on each of the ultrasound images of the plurality of frames, and
upon confirming failed region where pressing of the ultrasound probe against the subject is insufficient in the ultrasound image based on an edge clarity of the urinary bladder region in the ultrasound image, determine that the ultrasound image is of a failed frame.

5. The ultrasound diagnostic apparatus according to claim 1, wherein the processor is further configured to: perform image analysis on each of the ultrasound images of the plurality of frames, and upon confirming failed region where pressing of the ultrasound probe against the subject is insufficient in the ultrasound image based on an edge clarity of the urinary bladder region in the ultrasound image, determine that the ultrasound image is of a failed frame.

6. The ultrasound diagnostic apparatus according to claim 2, wherein the processor is further configured to, upon confirming the failed region is in the ultrasound image but the urinary bladder region does not overlap the failed region, determine that the rescan with the ultrasonic beam is not needed.

7. The ultrasound diagnostic apparatus according to claim 3, wherein the processor is further configured to, upon confirming the failed region is in the ultrasound image but the urinary bladder region does not overlap the failed region, determine that the rescan with the ultrasonic beam is not needed.

8. The ultrasound diagnostic apparatus according to claim 4, wherein the processor is further configured to, upon confirming the failed region is in the ultrasound image but the urinary bladder region does not overlap the failed region, determine that the rescan with the ultrasonic beam is not needed.

9. The ultrasound diagnostic apparatus according to claim 5, wherein the processor is further configured to, upon confirming the failed region is in the ultrasound image but the urinary bladder region does not overlap the failed region, determine that the rescan with the ultrasonic beam is not needed.

10. The ultrasound diagnostic apparatus according to claim 1, further comprising:
the ultrasound probe; and
a pressure sensor device attached to the ultrasound probe and configured to detect a contact pressure of the ultrasound probe against the subject, wherein
the processor is further configured to determine whether or not each of the ultrasound images of the plurality of frames is of a failed frame, based on the contact pressure of the ultrasound probe detected by the pressure sensor device.

11. The ultrasound diagnostic apparatus according to claim 1, further comprising: the ultrasound probe; and a pressure sensor device attached to the ultrasound probe and configured to detect a contact pressure of the ultrasound probe against the subject, wherein the processor is further configured to determine whether or not each of the ultrasound images of the plurality of frames is of a failed frame, based on the contact pressure of the ultrasound probe detected by the pressure sensor device.

12. The ultrasound diagnostic apparatus according to claim 1, wherein the processor is further configured to notify the user of a portion of the ultrasound probe that is not in contact with the subject or a portion of the ultrasound probe of which pressing against the subject is insufficient.

13. The ultrasound diagnostic apparatus according to claim 1, wherein the processor is further configured to notify the user of a portion of the ultrasound probe that is not in contact with the subject or a portion of the ultrasound probe of which pressing against the subject is insufficient.

14. The ultrasound diagnostic apparatus according to claim 2, wherein the processor is further configured to notify the user of a portion of the ultrasound probe that is not in contact with the subject or a portion of the ultrasound probe of which pressing against the subject is insufficient.

15. The ultrasound diagnostic apparatus according to claim 1, wherein
the processor is further configured to, upon determining at least one of the plurality of frames is a failed frame, issue a warning to the user.

16. The ultrasound diagnostic apparatus according to claim 1, wherein the processor is further configured to, upon determining at least one of the plurality of frames is a failed frame, issue a warning to the user.

17. The ultrasound diagnostic apparatus according to claim 2, wherein
the processor is further configured to, upon determining at least one of the plurality of frames is a failed frame, issue a warning to the user.

18. A method for controlling an ultrasound diagnostic apparatus, comprising:
acquiring ultrasound images of a plurality of frames through a scan with an ultrasonic beam on a subject using an ultrasound probe;
extracting a urinary bladder region from each of the ultrasound images of the plurality of frames;
calculating a feature quantity related to a size of the urinary bladder region extracted for each of the ultrasound images of the plurality of frames;
determining whether or not each of the ultrasound images of the plurality of frames is of a failed frame for which the scan with the ultrasonic beam on the subject has failed;
determining whether or not a rescan with the ultrasonic beam is needed, based on a time-series change in the feature quantity and position on a time axis of the ultrasound image of the frame determined to be the failed frame;
upon determining that the rescan with the ultrasonic beam is needed, recommending the rescan with the ultrasonic beam to a user;
receive a selection of whether or not to perform the rescan with the ultrasonic beam, in accordance with an input operation performed by the user via an input device;
upon determining that the rescan with the ultrasonic beam is not needed,
selecting an ultrasound image of a measurement frame that serves as a target subjected to measurement from among the ultrasound images of the plurality of frames, based on the feature quantity;
analyzing the ultrasound image of the measurement frame; and
calculating a urine volume in the selected ultrasound image of the measurement frame.

* * * * *